US012385856B2

United States Patent
Leung et al.

(10) Patent No.: US 12,385,856 B2
(45) Date of Patent: Aug. 12, 2025

(54) SUCTION-CONTROLLABLE TRIAXIAL TEST SYSTEM FOR STUDYING THE MICRO-HYDROMECHANICAL BEHAVIOR OF UNSATURATED SOILS WITH IN-SITU X-RAY MICRO COMPUTED TOMOGRAPHY SCANNING

(71) Applicant: The Hong Kong University of Science and Technology, Hong Kong (CN)

(72) Inventors: Kwan Anthony Leung, Hong Kong (CN); Jianbin Liu, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 566 days.

(21) Appl. No.: 17/661,917

(22) Filed: May 3, 2022

(65) Prior Publication Data

US 2023/0051767 A1  Feb. 16, 2023

Related U.S. Application Data

(60) Provisional application No. 63/183,079, filed on May 3, 2021.

(30) Foreign Application Priority Data

Aug. 10, 2021 (CN) .......................... 202110913361.5

(51) Int. Cl.
  *G01N 23/046* (2018.01)
  *G01N 3/12* (2006.01)
  (Continued)

(52) U.S. Cl.
  CPC ............. *G01N 23/046* (2013.01); *G01N 3/12* (2013.01); *G01N 23/083* (2013.01); *G01N 23/10* (2013.01); *G01N 33/24* (2013.01)

(58) Field of Classification Search
  CPC ...... G01N 23/046; G01N 3/12; G01N 23/083; G01N 23/10; G01N 33/24;
  (Continued)

(56) References Cited

U.S. PATENT DOCUMENTS 11,119,056 B2    9/2021  Wang et al.
2021/0055234 A1*  2/2021  Wang ................... G01N 23/046

FOREIGN PATENT DOCUMENTS

CN    109060851 A    12/2018
CN    110887738 A     3/2020
KR    10-1683620 B1  12/2016

OTHER PUBLICATIONS

Rampino, Celestino & Mancuso, Claudio & Vinale, Filippo. (2000). Experimental behaviour and modelling of an unsaturated compacted soil. NRC Research Press website. (Year: 2000).*

* cited by examiner

*Primary Examiner* — Timothy P Graves
(74) *Attorney, Agent, or Firm* — SALIWANCHIK, LLOYD & EISENSCHENK

(57) ABSTRACT

The subject invention pertains to a suction-controllable triaxial test system and a method for studying the micro-hydro-mechanical behavior of unsaturated soils through the visualization of the in-situ evolution of three-dimensional (3D) microstructure upon triaxial loading in a ($(p-u_a)$, q, s) space. The triaxial apparatus can be small enough to be operated within a micro-focus or nano-focus X-ray CT scanner. Internal characteristics and 3D movements of soil particles and the water and air in soil pores can be visualized during in-situ controllable hydro-mechanical loading processes without disturbing the soil sample. The evolution of 3D micro-structure of unsaturated soil samples of varying (Continued)

matric suction can be directly related with their element-scale behavior for conducting cross-scale fundamental studies.

21 Claims, 21 Drawing Sheets

(51) Int. Cl.
*G01N 23/083* (2018.01)
*G01N 23/10* (2018.01)
*G01N 33/24* (2006.01)

(58) Field of Classification Search
CPC ..... G01N 2203/023; G01N 2203/0232; G01N 2203/0242; G01N 2203/0256; G01N 2203/0641; G01N 3/02; G01N 3/06
See application file for complete search history.

SUCTION-CONTROLLABLE TRIAXIAL TEST SYSTEM FOR STUDYING THE MICRO-HYDROMECHANICAL BEHAVIOR OF UNSATURATED SOILS WITH IN-SITU X-RAY MICRO COMPUTED TOMOGRAPHY SCANNING

CROSS-REFERENCE TO RELATED APPLICATION

This application claims the benefit of U.S. Application No. 63/183,079, filed May 3, 2021 and Chinese Application No. 202110913361.5, filed Aug. 10, 2021, which are hereby incorporated by reference in their entirety including any tables, figures, or drawings.

BACKGROUND OF THE INVENTION

Global soil behavior is dependent upon stress path and stress state during hydro-mechanical (H-M) loading. Water retention ability of a soil, which can be characterized by a soil water retention curve (SWRC), can be relevant to its soil state (e.g., void ratio and pore size distribution) and stress condition (i.e., stress-dependent). Shear strength of soil samples with same initial soil condition can be affected by the water content (or matric suction) prior to shearing. Soil can be a granular material, of which the macroscopic H-M properties can be influenced by its micro-structures including strength and stiffness of solid particles, particle size distribution, particle morphology, void ratio, pore-water content, and pore-air content, etc. Studying the micro-structure and interaction among solid particles, pore water pressure, and pore air pressure can be a common advanced approach to conduct fundamental investigation of the global H-M behavior of soils. There exists therefore a need for improved methods that can be used for studying relations between micro-structure evolution and macroscopic H-M behavior.

A number of geotechnical systems and methods have been used to obtain the micro-structure change of soil samples during or post loading. Conventionally, the efforts that have been made include: (1) using Scanning Electron Microscope (SEM) technique and Mercury Intrusion Porosimetry (MIP) technique after mechanical and hydraulic loading, in which the soil sample has to be dried before micro-structural investigation and thus provide post-loading information of soil samples; (2) using magnetic resonance imaging (MRI) technique to measure the pore water distribution of samples during loading or post hydraulic loading, in which the imaging range can be dependent upon water distribution of the sample; (3) using Environmental Scanning Electron Microscope (ESEM) technique to capture micro-structures of samples during hydraulic loading, which can be an in-situ imaging technique that allow direct observation and measurement of particles, micro pores, and pore water distribution of soil samples. The results obtained so can reflect 2D measurements of the surface morphology of soil samples.

An alternative imaging technique can be application of X-ray Computer Tomography (CT), which can be capable of capturing both the surface and internal three dimensional (3D) micro-structures of soil samples. In related art, a variety of instruments have been developed by researchers to study the evolution of micro-structures under certain loading paths. Wang et al. 2019 developed an X-ray transparent container that allows 3D visualization of pore water, air, and solid phases of wet soils (sample size: 10 mm in diameter and 10 mm in height). Manahiloh and Meehan 2017 developed an apparatus capable of controlling wetting-drying path of tested sample (sample size: 12 mm in diameter) in a range of 0-2.059 kPa by applying the hanging column method. Mohsin et al. 2020 reported an apparatus capable of wetting-drying path controlling of tested sample (sample size: 25.4 mm in diameter and 38.1 mm in height) in a range 0-3.5 kPa by applying water head control method and using a microporous membrane. Khaddour et al. 2018 developed an apparatus capable of controlling wetting-drying path of tested sample (sample size: 10 mm in diameter and 10 mm in height) in a range of 0-7 kPa by applying the hanging column method. Higo et al. 2013 reported a triaxial loading apparatus that can be able to shear unsaturated soil sample (sample size: 35 mm in diameter and 70 mm in height) under 50 kPa of confining pressure with no suction-control. Ando 2013, 2015 developed a triaxial loading system for shearing dry soil sample (sample size: 11 mm diameter and 22 mm height) with a maximum confining pressure of 400 kPa. Cheng and Wang 2018 reported a triaxial loading system for shearing dry soil sample (sample size: 8 mm in diameter and 16 mm in height) under high confining pressure of 1.5 MPa. Wang et al. 2019 developed an in-situ triaxial loading apparatus using back-pressure control method to control matric suction of tested sample (sample size: 10 mm in diameter and 20 mm in height) and achieved a matric suction control in a range of 0-4 kPa. These types of instruments and methods reported are typically classified as water evaporation setups (which allow water evaporation), matric suction controlled drying-wetting setups, uniaxial loading setups (wet or dry samples) without suction-control, triaxial loading setups (wet or dry samples) without suction-control, modified triaxial loading setups with limited suction-control (using back pressure) or water pressure monitoring (water saturated sample). The advancements of these existing methods and instruments used in conjunction with the in-situ X-ray CT imaging can effectively investigate 3D micro-structural evolution of samples during certain hydrological, mechanical, or H-M loading path.

BRIEF SUMMARY OF THE INVENTION

Experimentally measuring the interrelationships between the micro- (or pore) and macro (or element) scale using the same soil sample can be a superior research method to study and understand the behavior of unsaturated soil of varying degree of saturation or matric suction. The results obtained from such testing methods can directly and simultaneously quantify the 3D evolution of micro-structural characteristics and measure the elemental response of the soil sample. Specific research interests and concerns of such type of experimental investigation can characterise H-M behaviour of unsaturated soil, including (1) influence of soil void ratio and particle morphology on soil compressibility and consolidation properties; (2) influence of particle size distribution and particle shape on soil shearing behavior and soil water retention properties; (3) bonding effects of inter-granular meniscus water (or matric suction) on soil shear strength; (4) influence of hydraulic (e.g. wetting-drying) paths and mechanical (e.g. loading-unloading) paths on soil volume change, shearing and stress-dilatancy behavior; (5) and stress-dependent effects on soil water retention curve (SDSWRC) and its effect on the H-M behavior. In order to better address these cross-scale scientific problems, it can be beneficial to develop methods and design corresponding instruments that can be capable of flexibly controlling the mechanical and/or hydraulic loading paths and monitoring relevant parameters to obtain three-dimensional (3D) evolution of micro-structural characteristics of the sample simultaneously during in-situ loading process within the $(p-u_a)$-q-s space. In certain embodiments, the $(p-u_a)$-q-s can be defined and/or parameterized in terms of p, a confining pressure acting on the soil sample from radial direction, $u_a$, a pore air pressure, q, an axial mechanical load applied to the soil sample from a loading rod, and s, a matric suction pressure.

One remaining problem in the study of behavior of soil samples can be the lack of an instrument or method that allows flexible continuous controlling of multi-stress-path in $(p-u_a)$-q-s space and desired soil stress states relevant to the field condition or engineering problems of concern, as well as obtaining in-situ images at the same time during the control and application of hydrological, mechanical, or H-M loading process.

The reasons for prior inventions being unable to address the above problems include the following three contradictory factors: (1) the difficulty in applying wider range matric suction control techniques in a very limited instrument space, (2) difficulty in structural design of the components that need to balance both the size of the instruments and the functionality in freely continuous controlling of desired H-M stress paths and monitoring of relevant parameters such as pore water pressure and pore air pressure, and (3) difficulty in sample preparation and installation; the small sample size needs to be small enough to ensure a high full-field imaging resolution but it can be difficult to avoid sample disturbance in conventional sample preparation process, since miniature soil samples can be especially easy to be disturbed due to its low load bearing capacity.

In general, synergetic H-M loading technology and in-situ X-ray CT technology can be currently the most advanced and potential technology in investigating microscopic-macroscopic relations of geo-materials including soils of varying degree of saturation or matric suction.

Embodiments of the subject invention can provide a suction-controllable triaxial test system for concurrent in-situ loading and X-ray CT 3D visualization of geo-materials at both element and pore scales, and in certain embodiments a triaxial compression system that can be placed in an X-ray CT scanner, that allows for continuous control of hydro-mechanical loading paths, and that allows for in-situ visualization of 3D internal micro-structures of the sample at specified points in $(p-u_a)$-q-s space during loading without disturbing soil samples.

Embodiments provide a suction-controllable triaxial test system and a method for studying the micro-hydro-mechanical behavior of unsaturated soils through the visualization of the in-situ evolution of 3D microstructure upon triaxial loading in X-ray CT scanners. Related art systems for in-situ loading and imaging in X-ray CT scanners do not allow flexible and continuous control of the stress paths in $(p-u_a)$-q-s space for unsaturated soils. These systems also cannot obtain in-situ images of 3D microstructure and hence cannot study the micro-hydro-mechanical behavior of soil under combined H-M loading conditions.

Certain embodiments can provide a triaxial loading unit, an integrated cell pressure and suction-control unit, a strain-controlled axial loading unit, and a sample preparation and installation unit. These units can be tailored-designed to be small in size so they can be placed in an X-ray CT scanner for in-situ scanning and imaging. One embodiment of the present invention provides a high Air-Entry-Value (AEV) ceramic disk for controlling a wider range of matric suction of an unsaturated soil sample and also a water reservoir for measuring the soil water content and degree of saturation. Embodiments can provide a specific design of the loading rod within the triaxial loading unit for simultaneous application of axial loading, air pressure for application of confining pressure, and air pressure for application of matric suction when using the axis-translation technique. Embodiments can also provide a set of components for non-disturbing sample preparation and sample installation. Embodiments provide tailor-designed pressure controlling subsystem for regulating air pressure and a stepping motor controller for precise strain control during mechanical loading. Miniature sensors can be mounted in the subsystem for continuously monitoring the soil responses including pore air pressure, pore water pressure, axial displacement, and axial force. Sensors can be connected to a specified software for simultaneous, parallel, serial, synchronous, or asynchronous data recording and processing.

Embodiments can provide a suction-controllable miniature triaxial apparatus or system and a method for measuring the micro-hydro-mechanical behavior of unsaturated soils through the visualization of 3D microstructure evolution upon triaxial loading in X-ray CT scanners. Certain embodiments can comprise a triaxial loading unit, an integrated cell pressure and suction-control unit, a strain-controlled axial loading unit, and a sample preparation and installation unit. These units can be miniature (e.g., generally less than 450 mm in height and 120 mm in diameter and 10 kg in weight) in size so they can be placed in an X-ray CT scanner for in-situ scanning and imaging upon triaxial loading. Embodiments can provide a high air-entry value ceramic disk for controlling soil matric suction of up to 500 kPa via two independent suction-controlled systems, for example the hanging column technique (e.g., 0-10 kPa) and the axis-translation technique (e.g., 10-500 kPa). Certain embodiments are also equipped with a water reservoir for precisely and accurately measuring changes in soil water content and degree of saturation. A loading rod can be tailor-designed with unique structure and geometry for achieving simultaneous applications of axial loading, air pressure for controlling confining pressure, and air pressure for controlling matric suction in a limited space. Embodiments can provide a set of components for non-disturbing sample preparation and installation. In certain embodiments, miniature sensors can be mounted in the apparatus or system for continuously monitoring pore air pressure, pore water pressure, axial strain, and axial force.

Embodiments provide a suction-controllable triaxial system or apparatus and a method for studying the micro-hydro-mechanical behavior of unsaturated soils through the visualization of the in-situ 3D microstructure evolution upon triaxial loading in $(p-u_a)$-q-s space. The apparatus can have two independent subsystems; (1) strain-controlled mechanism (i.e., applying a mechanical load by controlling a constant rate of axial displacement to the sample) to apply triaxial compression or extension loading up to 5 MPa to a soil sample and (2) an integrated suction-control unit to apply hydraulic loading in terms of matric suction. The suction-control unit can switch between a hanging column module for applying matric suctions less than 10 kPa and an axis-translation module for matric suctions ranged between 10-500 kPa. The apparatus can be tailor-configured (i.e., with a unique structural, geometric, and ratio-driven designs of components in this assembly; the apparatus can be further downscale or upscale to fit most of the chamber of X-ray CT scanners available in the market without sacrificing the functionality of the apparatus) so it can be mounted on top of the rolling stage in an X-ray CT scanner and connected to a software for continuous remote-control and data acquisition. An instrument for a suction-controllable triaxial compression apparatus specifically developed for an X-ray CT scanner can include a sample stage that embeds a high AEV ceramic and a water reservoir, an X-ray transparent triaxial chamber with a special designed loading rod configured and adapted for simultaneous axial loading, pore air pressure sealing and confining pressure sealing, a strain-controlled axial loading component, and a set of components for in-situ non-disturbing sample preparation sample installation. Embodiments can be small enough (e.g., generally less than 450 mm in height and 120 mm in diameter and 10 kg in weight) to be able to be put into a micro-focus or nano-focus X-ray CT scanner. Embodiments can provide a portable and self-contained apparatus that can be independent of specific types or models of X-ray CT scanners. With the development of the triaxial apparatus, 3D movements of soil particles and the water and air in soil pores can all be visualized during an in-situ controllable H-M loading process without disturbing the soil sample. Utilizing certain systems and methods of embodiments of the subject invention, evolution of 3D micro-structure of any unsaturated soil samples of varying matric suction can be directly related to their element-scale behavior for conducting cross-scale fundamental studies, which are unable to be achieved by other inventions.

DETAILED DISCLOSURE OF THE INVENTION

Figure 1:
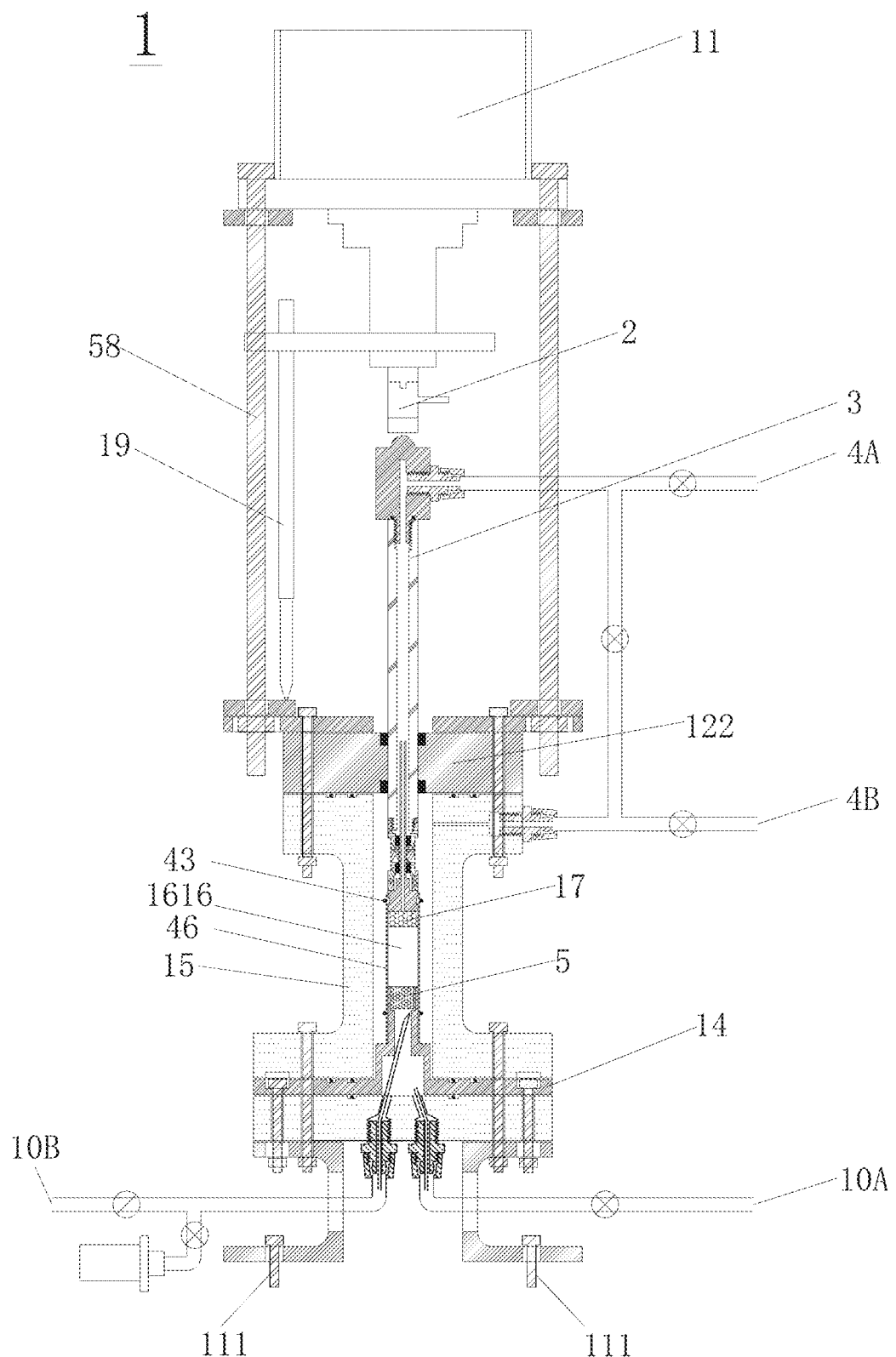
FIG. 1 is a schematic diagram of a triaxial loading unit according to an embodiment of the subject invention.

While the various embodiments used in the present invention are discussed in this description, it should be appreciated that many relevant inventive concepts can be embodied in various specific contexts of the present invention. The specific embodiments discussed herein are merely illustrative of specific ways to make and use the invention and do not delimit the scope of the invention.

To facilitate the understanding of this disclosure, a number of terms are defined in the description. Terms defined herein have meanings as commonly understood by a person of ordinary skill in the area relevant to the present disclosure. Terms such as "a", "an", and "the" are not intended as reference to only a singular entity, but may include the general class to which a specific entity refers. Terms for the specific embodiments described herein are merely for the purpose of the invention, however, their usage does not delimit the invention, except as outlined in the claims.

The term "$(p-u_a)$-q-s space" used herein denotes a stress space described in a three dimensional Cartesian coordinate system where axes p, q, and s are mutually orthogonal. The symbols p, $u_a$, q, and s represent mean total stress (p), pore air pressure ($u_a$), deviatoric stress (q, also called as shear stress), and matric suction (s) experienced by a soil sample, respectively. The term $(p-u_a)$ denotes net mean stress. The term "stress path" used herein represents the direction, magnitude and sequence of $(p-u_a)$, q, and s experienced by a soil sample in the $(p-u_a)$-q-s space. The terms "in-situ loading" and "in-situ scanning and imaging" used herein means that the hydro-mechanical loading can be conducted inside a CT scanner with X-ray on, that both the loading and imaging are conducted to the same sample simultaneously during an experiment, and that the 3D microstructure of soil samples can be scanned and imaged simultaneously under controlled loading conditions.

Embodiments of the present invention can provide a system and a method that can flexibly and continuously control the loading conditions of soil samples in the $(p-u_a)$-q-s space, while at the same time conducting in-situ scanning and imaging of the 3-D microstructure evolution of unsaturated geomaterials. The combined used of the triaxial loading technology and the X-ray CT imaging technology makes certain embodiments of the invention highly novel and original, while providing the capability to simultaneously study both the microscopic and macroscopic hydro-mechanical behavior of unsaturated geomaterials. Certain embodiments can provide measurement and analysis of fundamental macro-micro trans-scale mechanics of materials under complex loading conditions.

Embodiments can provide a suction-controllable triaxial test system that can be a self-contained system that integrates a triaxial loading unit, an integrated cell pressure and suction-control unit, and a sample preparation and installation unit. The triaxial loading unit can comprise an assembly of key components, namely, a novel sample stage connected to an integrated suction-controlled unit, a triaxial chamber, and a strain-controllable axial loading component. Embodiments can independently control the net mean stress and matric suction (which are two stress-state variables governing the behavior of unsaturated geomaterials), and also the effects of these two variables on deviatoric stress. Embodiments can be designed to provide a self-contained system (e.g., a system that has its own hardware and software thus can independently operate) that can be independent of specific types or models of X-ray CT scanners in the market. The dimension of the invention can be adjusted in various embodiments according to the needs of integrating into specific types or models of X-ray CT scanners.

Figure 2:
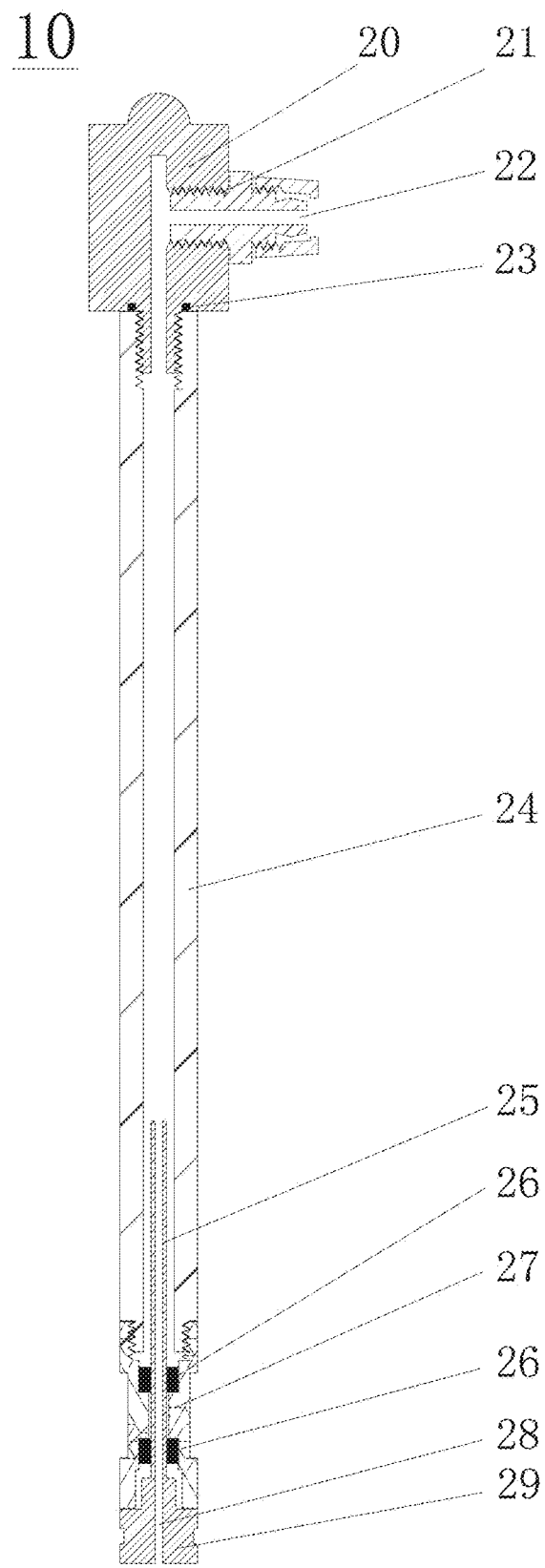
FIG. 2 is a schematic diagram showing a loading rod assembly according to an embodiment of the subject invention.
Figure 3:
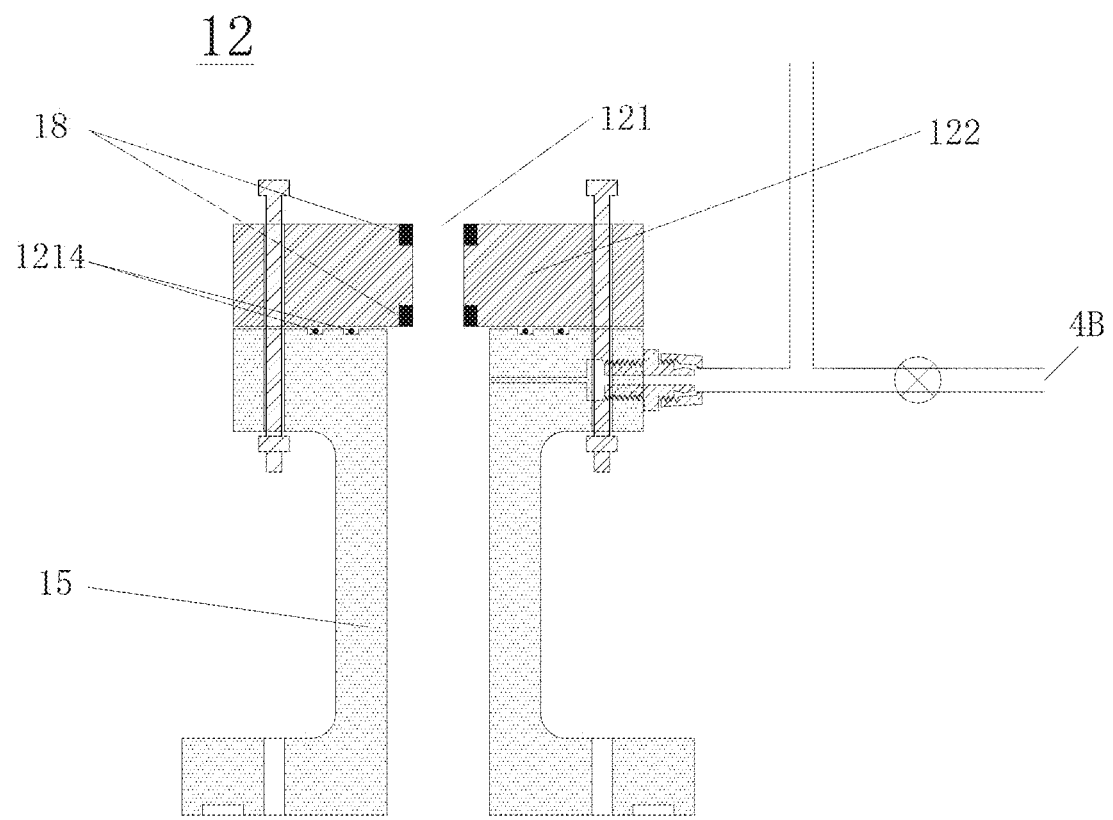
FIG. 3 is a schematic diagram showing an X-ray transparent chamber and chamber cap according to an embodiment of the subject invention.
Figure 4:
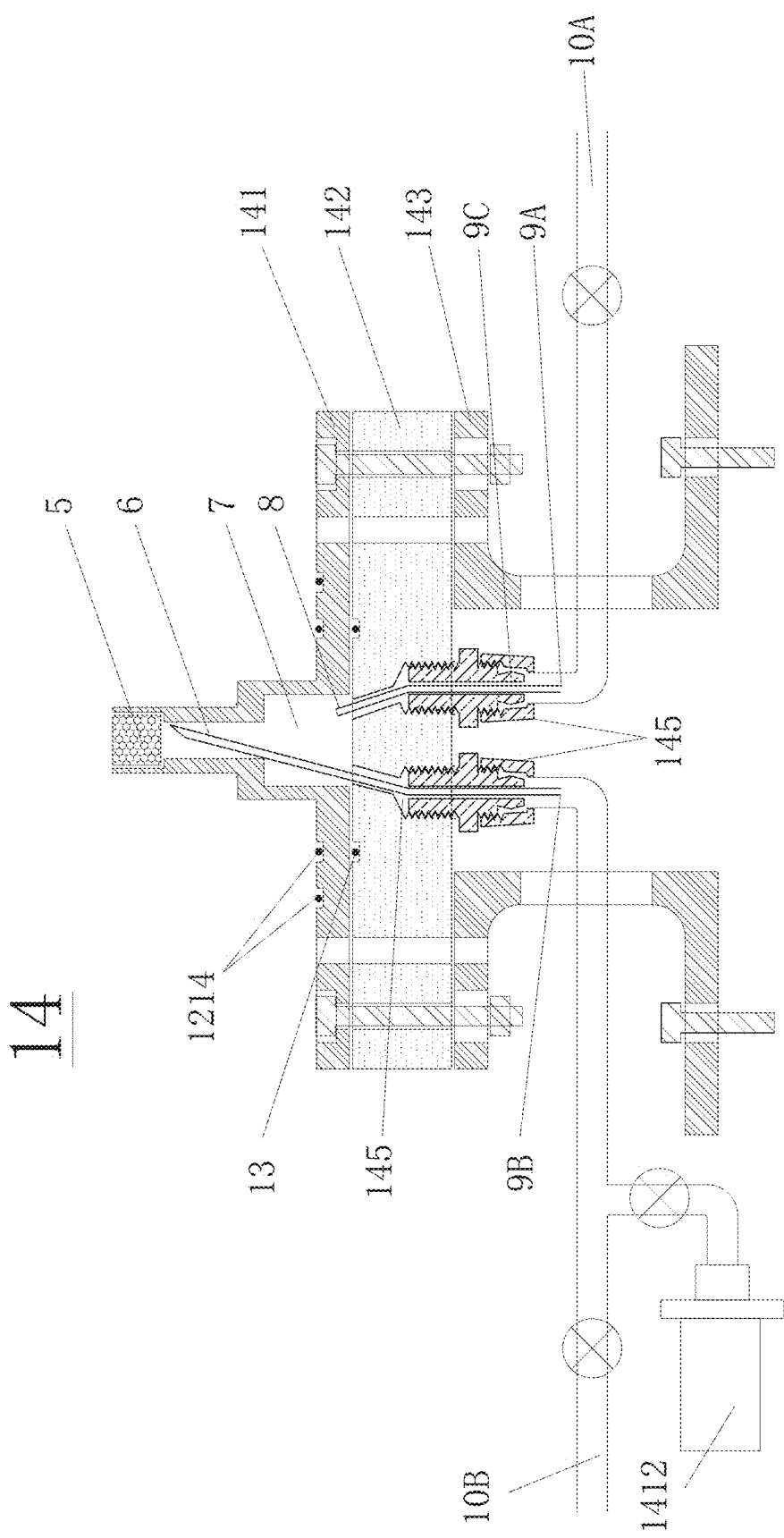
FIG. 4 is a schematic diagram showing a sample stage structure according to an embodiment of the subject invention.
Figure 5:
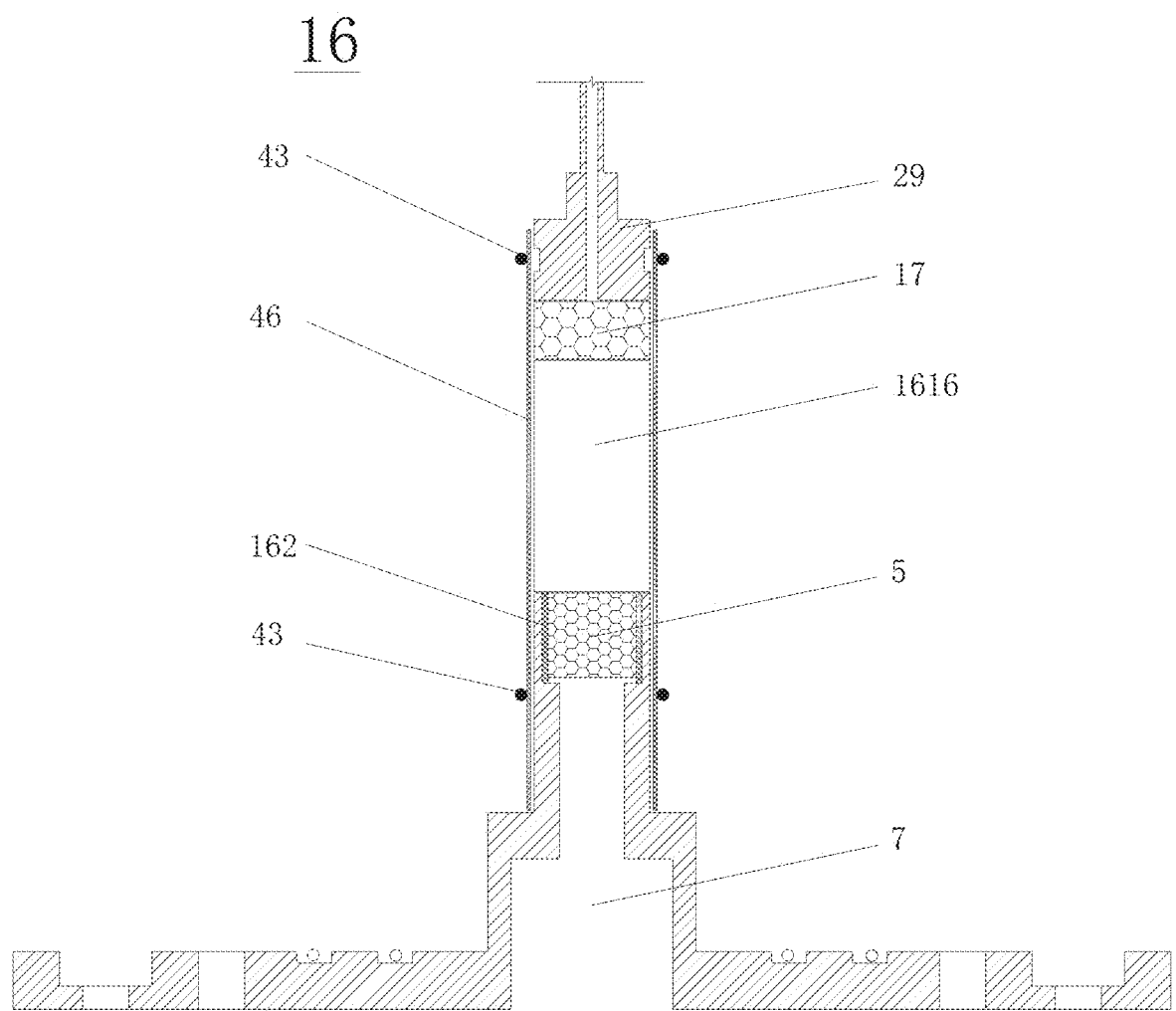
FIG. 5 is a schematic diagram showing a soil sample installation according to an embodiment of the subject invention.
Figure 6:
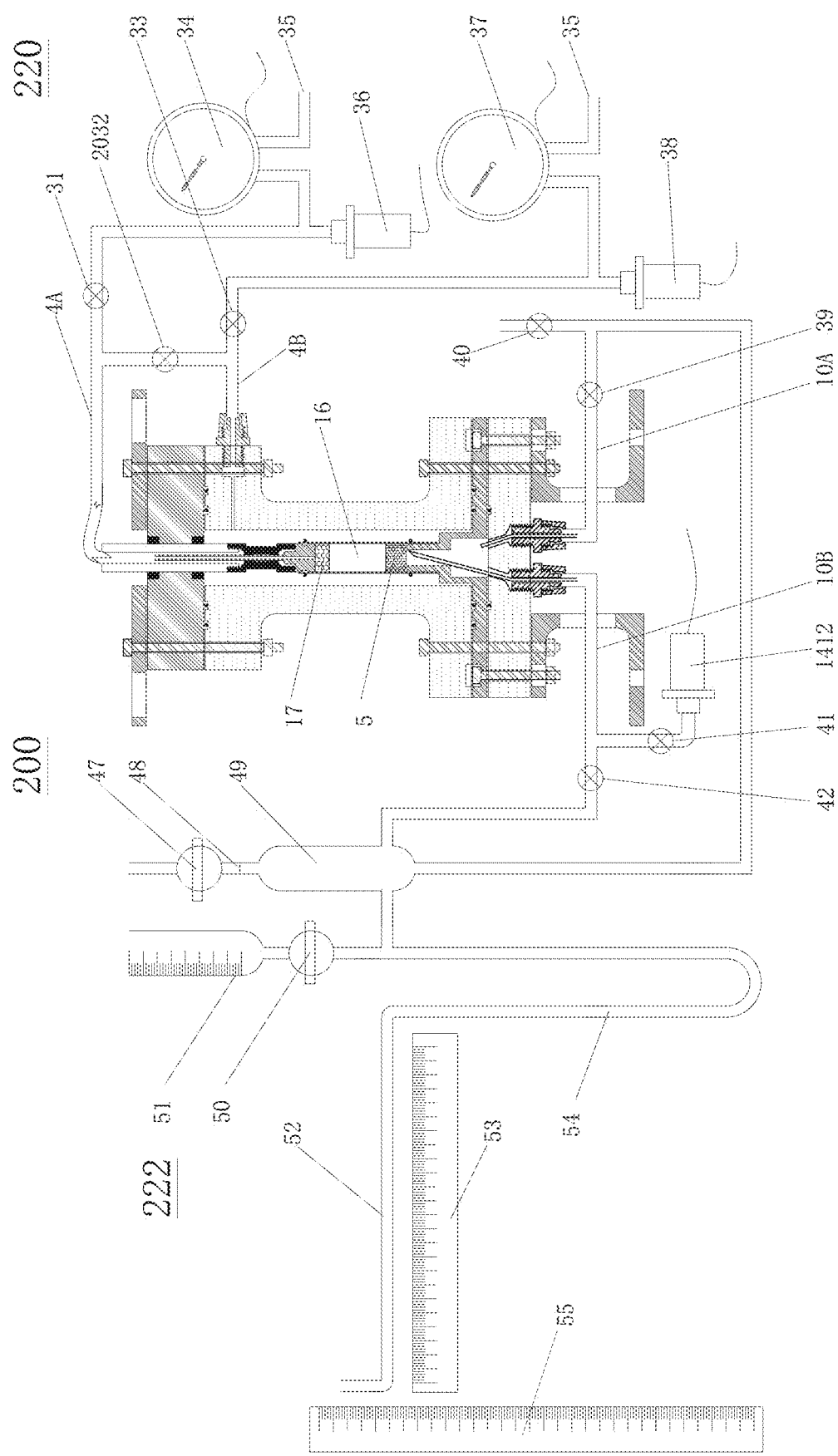
FIG. 6 is a schematic diagram showing an integrated cell pressure and suction-control unit including cell pressure controlling components, hanging column module, and axis-translation module of a suction-controllable triaxial test system according to an embodiment of the subject invention.
Figure 7:
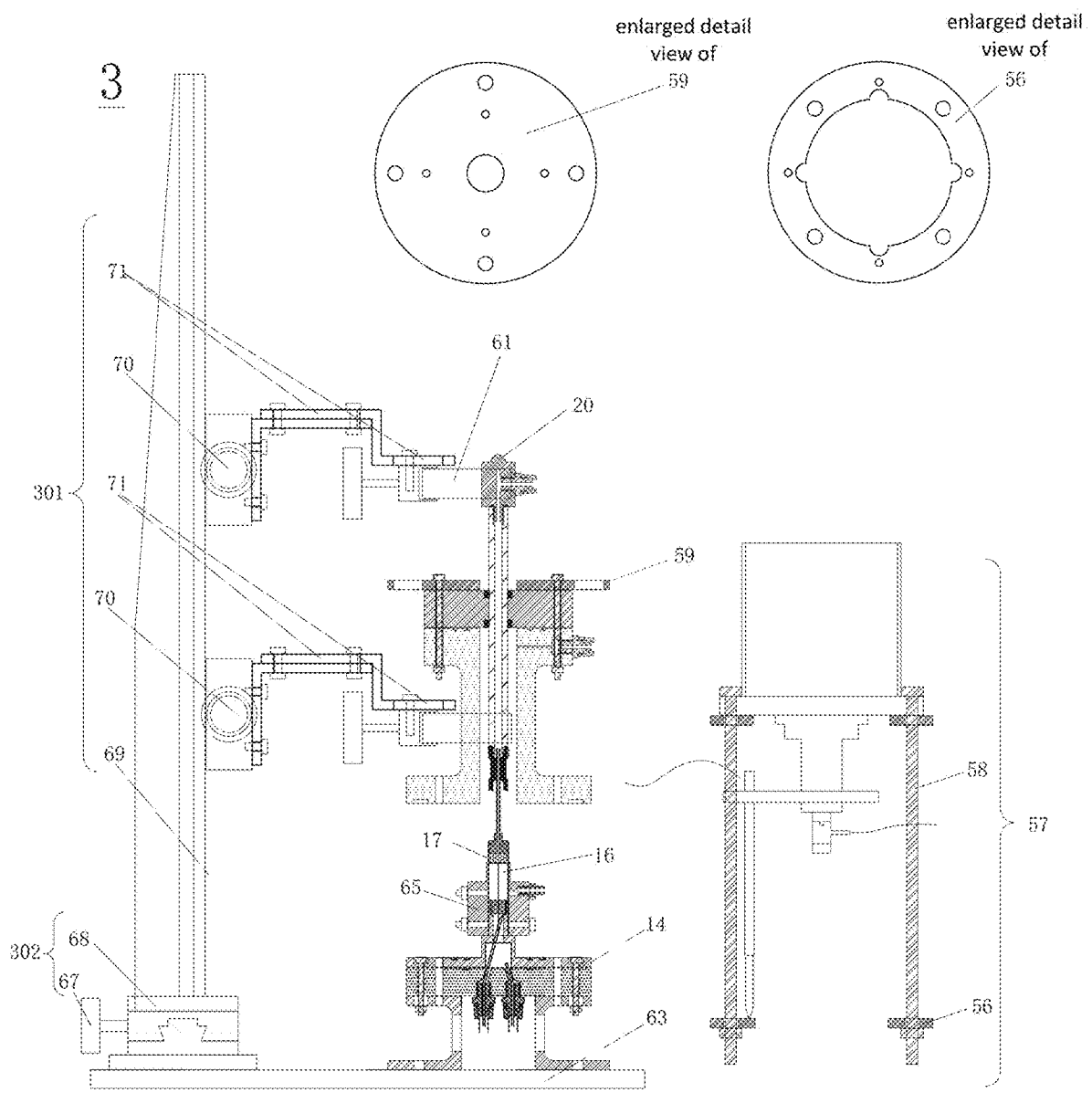
FIG. 7 is a schematic diagram showing a sample preparation and installation unit configured and adapted to assemble and install a sample on a sample stage structure of a triaxial loading unit according to an embodiment of the subject invention.
Figure 8A:
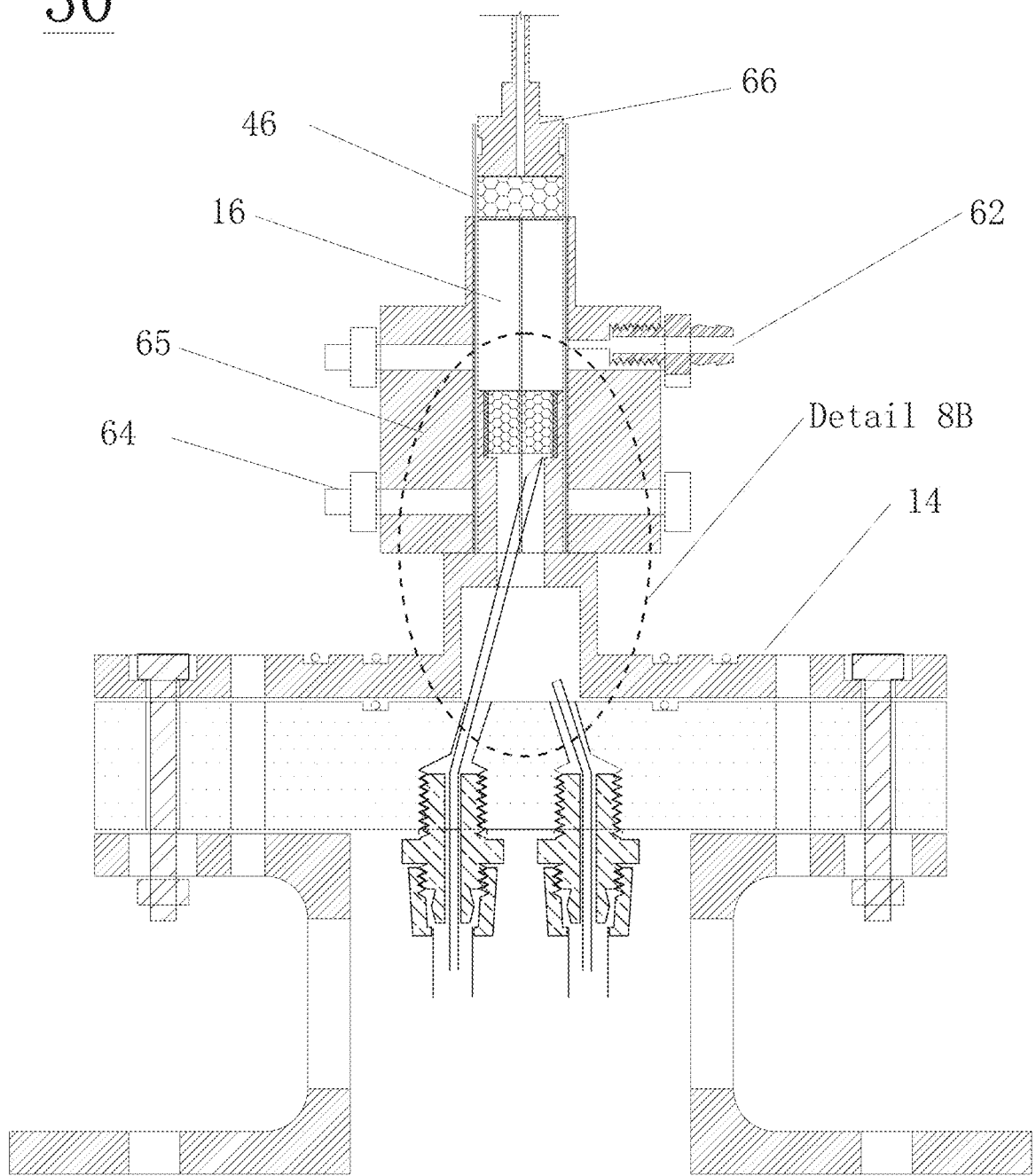
FIG. 8A is a schematic diagram showing the usage state of a mold for sample preparation in a suction-controllable triaxial test system according to an embodiment of the subject invention.
Figure 8B:
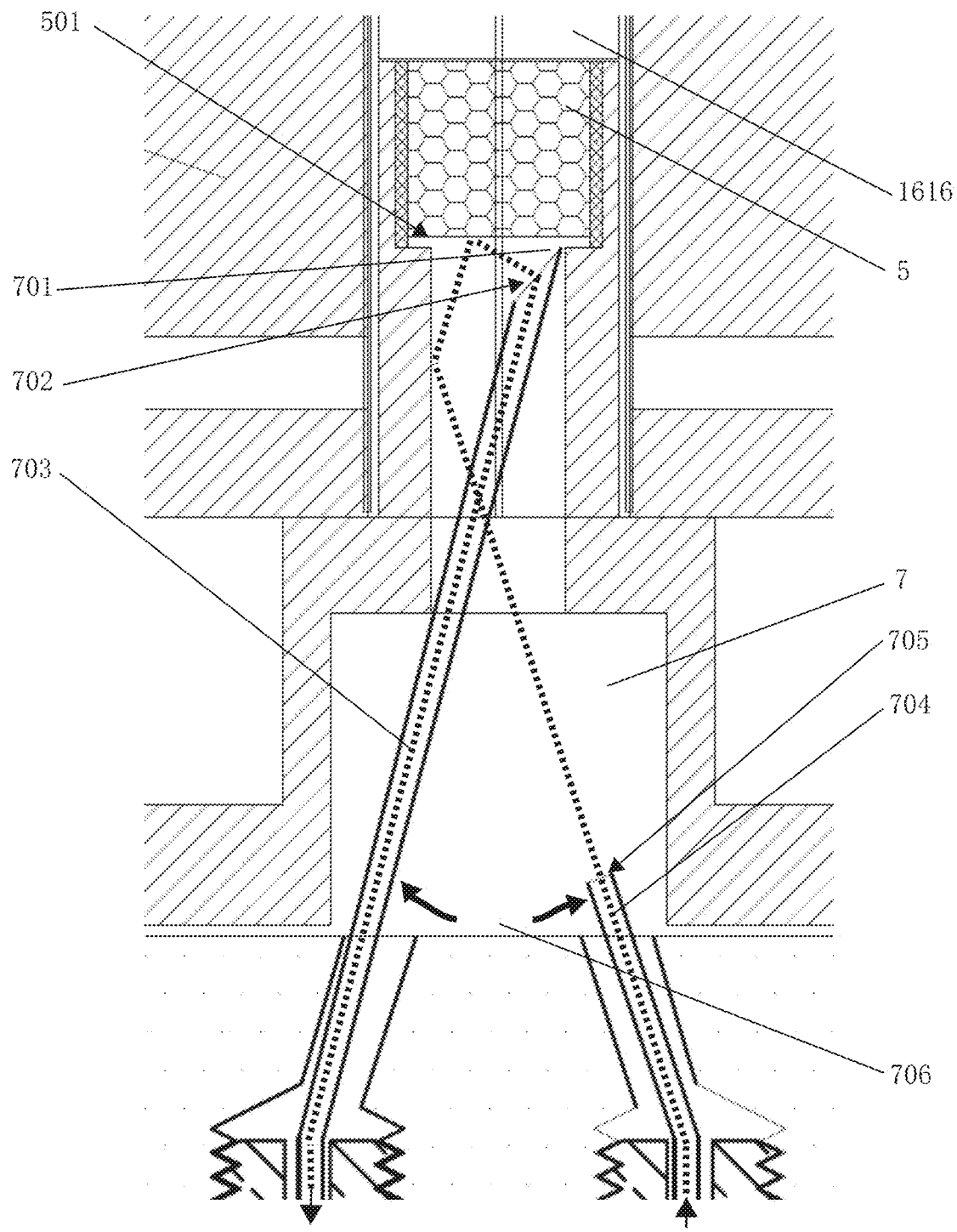
FIG. 8B is a detailed view showing the reservoir, inlet, and outlet according to an embodiment of the subject invention.
Figure 8C:
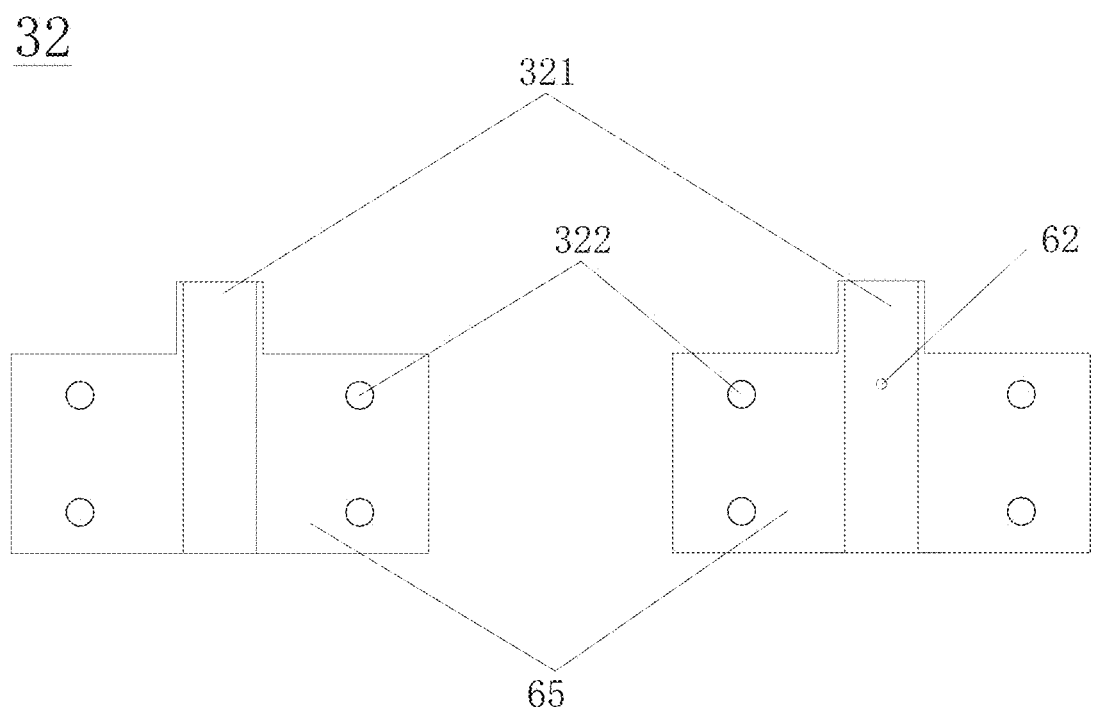
FIG. 8C is a schematic diagram showing the structure of the unfolding mold in a suction-controllable triaxial test systems according to an embodiment of the subject invention.
Figure 9:
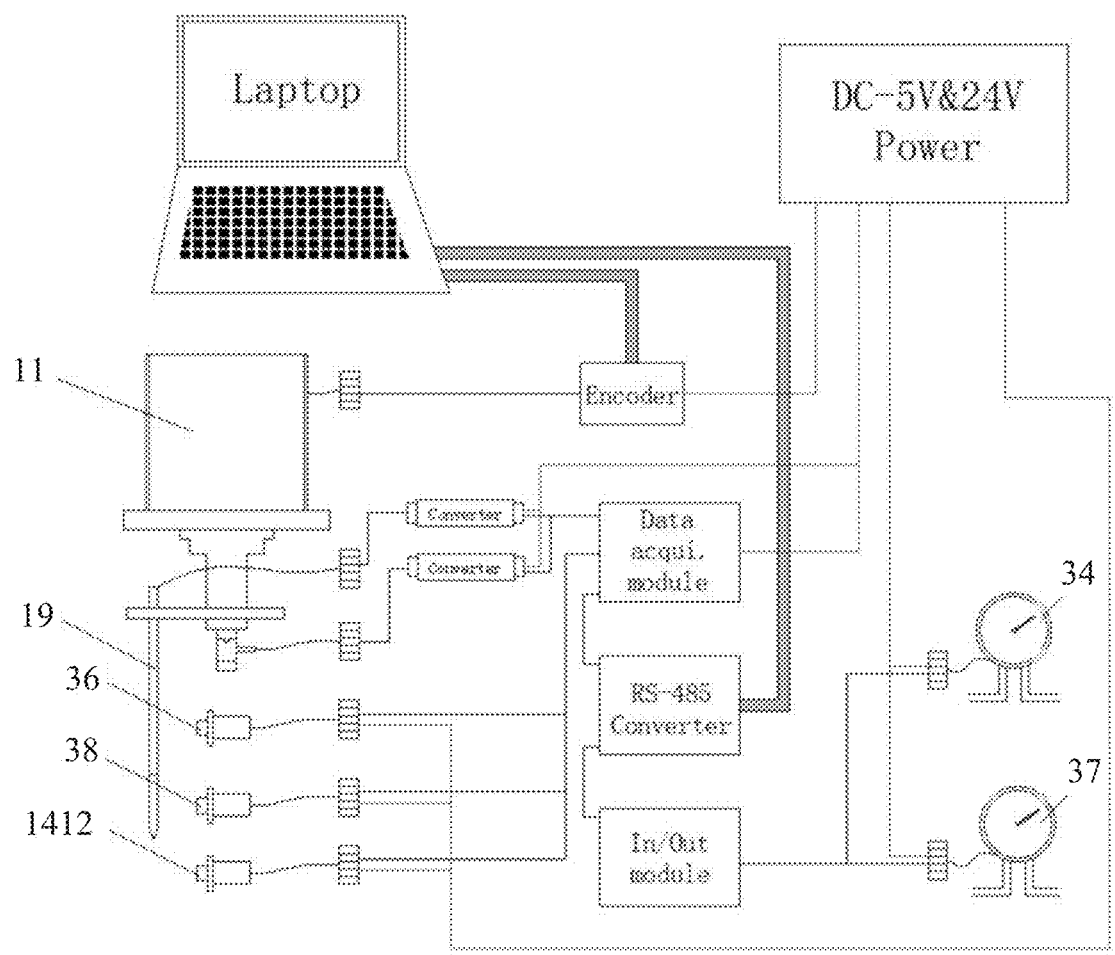
FIG. 9 is a schematic diagram that shows an experimental setup including a data acquisition module according to an embodiment of the subject invention.

FIG. 1 shows a full assembly of selected key components for a triaxial loading unit. FIG. 2 depicts a detailed view of the tailor-designed loading rod. FIG. 3 shows the detailed design of an X-ray transparent chamber and chamber cap components' structure. FIG. 4 shows the detailed design of a sample stage structure. FIG. 5 shows the details of sample installations. FIG. 6 shows the detailed design of an integrated cell pressure and matric suction-control unit for wider range of suction-control and application, and the cell pressure controlling of the strain-controllable loading unit. FIG. 7 shows the detailed design of certain components made for sample preparation and installation in the triaxial apparatus. FIG. 8A shows the usage state of the mold for sample preparation, FIG. 8B shows details of water supply and return in the reservoir below a sample, and FIG. 8C shows the structure of the unfolding mold. FIG. 9 shows an experimental setup including a data acquisition module according to an embodiment of the subject invention.

FIG. 1 shows a schematic diagram of a triaxial loading unit 1 according to an embodiment of the subject invention. FIGS. 2-5 show the detailed structure designs of different components in FIG. 1. The assembly in this embodiment comprises a high resolution servo-controlled stepping motor 11 supported by threaded rods 58 and comprising a mechanism (e.g., a ball screw, a rack and pinion, or a linkage) to convert rotation to linear motion to apply axial strain, a high accuracy load cell 2 to monitor sample stress, a high accuracy Linear Variable Differential Transformer (LVDT) 19 to monitor sample strain, a loading rod 3 for axial force transmission, an X-ray transparent chamber 15 to retain confining pressure, a chamber cap 122 with two concentric radial seals 18 maintains confining pressure and allows the loading rod 3 to travel up and down vertically through hole 121, a sample stage 14 embedded with a high AEV ceramic 5 that allows water passing while prohibiting air passing, a water reservoir 7 for water supply, and a high accuracy water pressure transducer 1412 that allow negative and positive pressure monitoring. The gaps between the X-ray transparent chamber 15 and the chamber cap 122 and also the gaps between the chamber 15 and the sample stage 14 can be each sealed, respectively, by two pairs of concentric O-rings 1214 so the unit can be airtight to a high degree. The chamber 15 and the loading rod 3 can be connected to a set of air pressure controlling units 4A and 4B for regulating the magnitude of confining pressure and pore-air pressure applied to a soil sample. A low AEV porous ceramic stone 17 can be placed between the loading rod 3 and the surface of soil sample 1616. A high AEV ceramic disk 5 can be placed below the soil sample 1616. The base of the ceramic 5 can be connected to a water reservoir 7 and a pair of small-diameter tubes (6 and 8, external diameter, e.g., of 1.8 mm). The longer tube 6 can be used to flush any diffused air in the system, while the shorter tube 8 can be used for water supply to the reservoir 7. The gap between the upper 141 and the middle 142 parts of the sample stage 14 (FIG. 4) can be sealed by an O-ring 13 to form a water-tight environment. Lower part 143 aligns and supports middle part 142. A pair of tubes (9A and 9B, internal diameter of 2.8 mm) can be provided to connect the reservoir 7 to water volume measurement and water pressure controlling components via 10A and 10B. In order to provide a bubble flushing procedure, a novel double tube connection structure 9C can be designed and gaps 145 between the tubes, joints, and pedestals can be filled with a glue such as epoxy. The sample stage can be bolted (e.g., by four screws) to form an entity. The whole assembly of the triaxial loading unit shown in FIG. 1 can be bolted on top of the rolling stage inbuilt in an X-ray CT scanner. The assembly can be miniature in size (i.e., 450 mm in height and not larger than 120 mm in diameter) to facilitate the installation of a soil sample and to minimize the chance of collision between the assembly and any part of an X-ray CT scanner during the spinning of the soil sample in a scanning process. The loading rod 3, soil sample 1616, and the upper surface of the sample stage 14 have the same diameter of 10 mm, while the sample 1616 can be 20 mm in height. Bolts 111 can be configured and adapted to mount the sample stage (e.g., to the sample preparation and installation unit or to an X-ray CT scanner.)

An embodiment of the subject invention provides the design of loading rod assembly 10, the details of which are shown in FIG. 2. The loading rod can be designed to provide axial loading and to retain the cell air pressure 45 and the air pressures inside the soil sample 1616 simultaneously. The loading rod unit comprises a cap 20, a joint 21 connected to a tube 22 that leads to an external air pressure source for applying the axis-translation technique to control matric suction of soil samples, a hollow shaft 24 of loading rod 3 with a smooth exterior surface to minimize friction, a connector 27 embedded with an upward radial seal 26 (1.8 mm in internal diameter) and a downward radial seal 28 (1.8 mm in internal diameter) and a movable sample cap 29 that can travel up and down vertically without air leakage. The hollow shaft 24 of loading rod 3 can be screwed to the cap 20 with an O-ring 23 utilized to inhibit air leakage at the contact. The connector 27 can be screwed to the hollow shaft 24 of loading rod 3 and a thin layer of vacuum grease can be applied to the contact to further inhibit air leakage. The radial seal 26 and the radial seal 28 inhibit leakage of air in the hollow shaft 24 of loading rod 3 and in the X-ray transparent chamber 15, respectively. The hollow sample cap 29 with a 40 mm long thin hollow part 25 (1.8 mm in external diameter) passing through the two radial seals can travel freely up and down. This design can be configured and adapted to move freely with the soil sample during consolidation upon an applied stress path. In this embodiment, a non-sealing interface at the contact between the connector 27 and the sample cap 29, allows the same air pressure to equalize in the space above the sample cap 29 and the rest of the chamber 15.

In an embodiment the integrated cell pressure and suction-control unit 200 comprises multiple pressure controlling components, selected details of which are shown in FIG. 6. These include confining pressure controlling components and suction-control components. The pressure controlling unit further comprises an air pressure controlling and monitoring unit 220 and a water pressure controlling and monitoring unit 222. In this embodiment the air pressure controlling and monitoring unit 220 has three valves (i.e., 31, 2032, and 33), a higher accuracy air pressure controller (e.g., resolution of 0.125 Pa with a range of 50 kPa, SMC, Japan) 34 for manual or automatic control of $u_a$, a high accuracy air pressure sensor (e.g., resolution of 0.125 Pa with a range of 50 kPa, Omega, USA) 36, a high range air pressure controller (e.g., resolution of 1.25 Pa with a range of 500 kPa, SMC, Japan) 37 for manual or automatic control of confining pressure and a high range air pressure sensor (e.g., resolution of 1.25 Pa with a range of 500 kPa, Omega, USA) 38. The controllers 34 and 37 are both connected to a high pressure air source (e.g., maximum of 700 kPa compressed air) 35. In one embodiment the water pressure controlling and monitoring unit 222 has four valves (i.e., 39, 40, 41 and 42), a water pressure sensor 1412 for measuring both negative and positive pressure, an air trap 49 with a level mark 48 and a valve 47, a burette 51 with a valve 50, a long flexible tube 54, a horizontal quartz tube 52 with a short level scale 53 and a vertically placed long scale 55. Prior to applying the air pressure or water pressure, soil sample 1616 can be prepared in a thin plastic membrane 46 and installed on the sample stage 14, to form a soil sample installation 16, where a high Air-Entry-Value ceramic disk 5 can be attached using epoxy 162 to inhibit leakage of both air and water. A pair of O-rings 43 can be installed on both ends of the soil sample so that the pressure within and outside the membrane can be independently controlled (FIG. 5).

Embodiments can provide integrated units for application of two or more suction-control techniques, namely, a hanging column technique and an axis translation technique, to achieve wider range control of matric suction (i.e., hydraulic loading) between 0 to 500 kPa precisely through two independent modules (e.g., the hanging column module and the axis-translation module). For controlling low matric suctions (e.g., 0-10 kPa), the hanging column module can be connected. To activate this module, a first valve 2032 can be off, while a second valve 31 can be on. The pressure controller 34 can be adjusted to connect to the atmospheric pressure. The horizontal quartz tube 52 can be placed at the same level as the upper surface of the ceramic disk 5.

Any air bubbles dissolved in the water reservoir can be flushed through connected tubes 703, 704. As shown in FIG. 8B water reservoir 7 extends up to lower surface 501 of high AEV ceramic 5. Although high AEV ceramic 5 inhibits flow of gasses, at higher pressures liquid flow can carry dissolved air bubbles from soil sample 1616 into water reservoir 7, where air bubbles can release upon a drop in pressure and become entrapped beneath lower surface 501 of high AEV ceramic 5. In the reservoir 7, the tubes 703 and 704 are arranged to form an effective bubble flushing system. Supply tube 704 is shorter and lower than return tube 703. The tip 701 of tube 703 with angled cut end 702 reaches to close proximity of lower surface 501 while tube 704 with plain end 705 extends only into the lower region of reservoir 7. The tube angle 706 between tube 703 and tube 704 is arranged to form a cross flow geometry such that the flow path is advantageously configured and adapted to effectively flush out bubbles concentrated at the top of reservoir 7 and near the lower surface 501.

In certain embodiments the tip 701 of tube 703 can be in contact with lower surface 501, alternatively in proximity to lower surface 501, including within 1 mm, alternatively within 0.5 mm, 0.25 mm, 0.1 mm, less than 0.1 mm, including increments and ranges thereof. In other embodiments the vertical distance between lower surface 501 and tip 701 can be a percentage of the vertical distance between tip 701 and end 705. For example, the vertical distance between lower surface 501 and tip 701 can be 20 percent of the vertical distance between tip 701 and end 705, alternatively 10, 5, 2, 1 percent, including increments and ranges thereof. In yet other embodiments the vertical distance between tip 705 and tip 701 can be advantageously designed to facilitate flushing of bubbles. For example, the vertical distance between tip 705 and tip 701 can be 100, 60, 30, 20, 10, or 5 mm, including increments and ranges thereof. Alternatively, the vertical distance between tip 705 and tip 701 can be a percentage of the vertical height or reservoir 7, for example 90 percent, 60, 30, 20, 10, or 5 percent, including increments and ranges thereof.

In certain embodiments the angle between lower surface 501 and cut end 702 can be advantageously designed to facilitate flushing of bubbles. For example, the angle between lower surface 501 and cut end 702 can be any geometrically feasible value (e.g., considering the relative angle of tube 703 approaching lower surface 501) including 5 degrees, alternatively 10, 20, 30, 40, 60, 70, 80, or 85, including increments and ranges thereof.

In certain embodiments the angle between a central axis of tube 703 and cut end 702 can be advantageously designed to facilitate flushing of bubbles (e.g., by providing a wider opening.) For example, the angle between a central axis of tube 703 and cut end 702 can be any geometrically feasible value (e.g., considering the relative length, diameter, and wall thickness of tube 703) including 15 degrees, alternatively 20, 30, 40, 60, or 75, including increments and ranges thereof.

In certain embodiments the angle 706 between a central axis of tube 703 and a central axis of tube 704 can be advantageously designed to facilitate flushing of bubbles (e.g., by aligning the flow path between the two tubes.) For example, the angle 706 between a central axis of tube 703 and a central axis of tube 704 can be any geometrically feasible value (e.g., considering the relative length of the tubes and the size of reservoir 7) including 15 degrees, alternatively 20, 30, 40, 60, or 75, including increments and ranges thereof.

The water level in air trap 49 can be adjusted to the level mark 48 and the valves 56 and 47 can be switched off. The position of water-air interface in tube 52 can be read by horizontal scale 53 and marked down and the water volume in burette 51 can be read. As part of a method in accordance with an embodiment of the subject invention, when the horizontal tube 52 can be moved downwards to a specified distance to control a desired matric suction, the height difference between the horizontal tube and the ceramic surface can be measured using the scale 55, in which every 100 mm indicates 1 kPa. The amount of water in tubes can be frequently adjusted to ensure the air-water interface can be always maintained in the horizontal tube 52. After equilibrium has been reached (e.g., the water air interface in tube 52 moved less than a specified amount for a specified period of time such as 12 hours for fine sand) the water-air interface position can be adjusted to the initial point and the volume change from burette 51 can be known. During the application of a hanging column technique, the pore water pressure can be in the sample negative while the pore air pressure can be atmospheric. For controlling high matric suctions (e.g., 10-500 kPa), the axis-translation module can be used. To activate this module, the valve 33 can be off, while the valves 31 and 2032 can be both on to release the pressure difference inside and outside the membrane 46. The horizontal quartz tube 52 can be put at the same level as the upper surface of the ceramic disk 5. In certain embodiments, the external air pressure applied by the controller 34 can be equal to the matric suction experienced by soil samples. During the application of the axis translation technique, the pore water pressure in the sample can be atmospheric while the pore air pressure can be positive. The criteria for matric suction equilibrium and volume change measurement can be the same as the previous procedures for applying a hanging column technique. The valve 41 can be closed when flushing air bubbles to inhibit them from entering into the pressure sensor 1412.

FIG. 9 shows stepping motor 11, LVDT 19, pressure sensors 36, 38, and 1412, and controllers 34 and 37 connected either directly or through appropriate converter, RS-485, or I/O modules to a data acquisition module. The data acquisition module is operably connected a laptop (or other computing device) which can host associated software to operate the data acquisition device, or various elements of the systems, units, apparatus, and devices of the subject invention. An encoder is shown connected directly to the laptop. The data acquisition module is also operably connected to DC power supply, the RS-485 converter, and the I/O module.

In one embodiment, for confining pressure control during consolidation or shearing, the valve 32 can be off to achieve separate control of matric suction and cell pressure 45. For undrained triaxial shearing, the valve 41 can be on but the valves 39 and 42, respectively, can be off during the mechanical loading process, the water pressure sensor 1412 can be used to continuously monitor any change in pore water pressures. For drained triaxial loading, the valve 39 and 40 are open for drainage of pore water in the tested sample.

Embodiments can advantageously provide a device used to prepare homogeneous soil samples of small volume and to install them in the triaxial system with minimum disturbance, e.g., as shown in FIG. 7. The device shown can be used to connect the three components of the triaxial loading unit, namely the sample stage component 14, chamber component (12 plus 59) and axial loading component 57. The device used for sample installation comprises a 300 mm by 300 mm baseplate (e.g., 304 stainless steel or 7075 aluminum, 10 mm thick) 63, a horizontal movement controllable sliding table 302 with a track 68 and a driver 67 (e.g., a hand wheel, a computer numerically controlled motor driven wheel, a manual controlled wheel with micrometer scale, a manual or computer numerically controlled stepping motor and a ball screw, a servo motor, or other motion control apparatus or mechanisms known in the art) to control horizontal movement of the horizontal sliding table, and vertical movement controllable sliding table 301 with a track 69 and one or more drivers 70 (e.g., two wheels) to control vertical movement of the vertical sliding table. Structures (e.g., one or more cantilever-shaped adjustable connectors) 71 are connected to the two control units as well as the clamps 61, which can be used to grasp the loading rod 3 by inserting the loading rod 3 in the grooves of the cap 20.

Embodiments can provide independent concentric travel of the loading rod 3 and the chamber 15, while the sample stage unit 14 can be moved freely in any horizontal direction. Soil samples can be prepared directly on top of the sample stage with a mold 65, which includes a hole 62, the hole 62 accessing an inner surface of cylindrical mold cavity 321, that connects to a vacuum pump to remove the air in between the membrane 46 and the internal surface of the mold. The two halves of the mold 65 can be advantageously joined and separated by installation of removal of bolts 64 through mounting holes 322. Prior to sample installation, the chamber unit 59 can be installed at desired vertical positions concentrically with the sample stage and loading rod as shown in FIG. 7. The soil sample 1616, together with the mold, can be moved to the plate 63. The sample stage component 14 can be adjusted to bring the components 12 and 14 to a concentric state. Then the loading rod 3 needs to be moved slowly downward to let the sample cap 66 gently touch the membrane 46 before locking the slide block and removing the mold. Then the chamber unit 59 can be moved downward to touch the sample stage 14 and block components 12 and 14 together. Finally, the clamp 61 can be released, the axial loading component 57 can be connected with each of components 12 and 14, respectively, and then the whole assembly of the triaxial loading unit (e.g., an assembly comprising components 14, 12, and 57) can be assembled to the rolling stage of an X-ray CT scanner.

Figure 10:
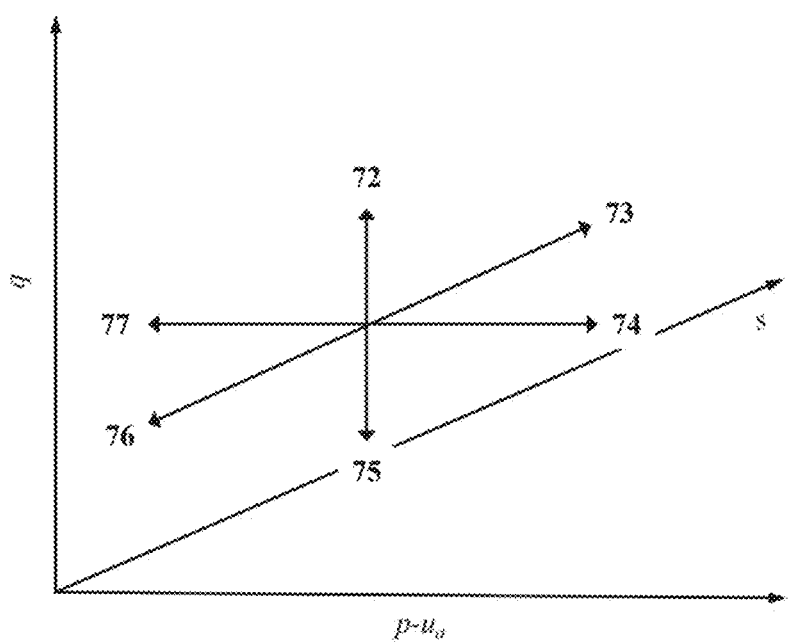
FIG. 10 is a schematic diagram showing certain possible controllable stress paths in triaxial $(p-u_a)$-q-s space according to an embodiment of the subject invention.

In certain embodiments the control of stress paths can refer to the control of variables p, which is net mean stress (i.e., $p=(\sigma1+\sigma2+\sigma3)/3-u_a$), q which is deviator stress (i.e. $q=\sigma_1-\sigma_3$), and s, which is matric suction (i.e., $s=u_a-u_w$), either individually or in combination. FIG. 10 is a schematic diagram showing one possible stress path that can be controlled by the specification of the ($p-u_a$)-q-s space. By controlling the matric suction through either a hanging column module or an axis-translation module, or both, soil samples can be subjected to either a drying (e.g., matric suction increase 73) or a wetting (e.g., matric suction decrease 76) path. Irrespective to the hydraulic loading path, soil samples can also be subjected to mechanical loading path, following isotropic loading 74 or unloading 77 paths to achieve a desired over consolidation ratio (an advantageously applied variable that can be used to better control the hydro-mechanical behavior of unsaturated soils). Deviatoric stress can be applied to the soil samples to undergo either a compression path (e.g., increasing q 72) or an extension path (e.g., decreasing q 75). Since the subsystems used to control the matric suction, isotropic loading/unloading, and shearing are independent from each other, embodiments allow for flexible control of stress paths to soil samples according to the testing needs. For example, to control the stress paths shown in FIG. 11, embodiments can decrease the matric suction by controlling the suction-control unit to achieve path 78→79; then increase the net mean stress by controlling the cell pressure controlling unit to achieve path 79→80; and finally increase the deviator stress by controlling the triaxial loading unit to achieve path 80→83. In certain embodiments, some or all of the foregoing steps can be completed in sequence (alternately, in parallel) and under in-situ, concurrent, or simultaneous X-ray CT scanning or imaging.

Embodiments can provide a suction-controllable triaxial test system and software for control and data acquisition. As mentioned, the system can be configured and adapted (e.g., be small, compact, and light enough) to be able to be installed on top of the rolling stage of X-ray CT scanners. Hence the full field micro-structures of tested sample can be simultaneously obtained during the controlled hydro-mechanical loading process. The software can be used to monitor, analyze, and control fluid pressure, deformation, and stress of tested sample, and also to control various embodiments of the compression system to achieve desired loading path manipulation of tested sample. The software can be installed on a computer, connected to the system and be able to collect, store, display, and export data. The software can be used to continuously control various components including stepping motor 11 and air pressure controllers 34 and 37 of the system. The software can be also used to continuously monitor various sensors of the triaxial loading unit, e.g., load cell 2, LVDT 19, and pressure sensors 36, 38, and 1412.

Materials and Methods

Embodiments of the subject invention address the technical problem of existing triaxial test sample loading apparatus control methods not being suitable for simultaneous or in-situ x-ray imaging during triaxial testing. This problem can be addressed by providing a triaxial testing control system, in which control synchronized with an X-ray CT scanning device can be utilized to produce in-situ X-ray imaging of samples at one or more specified points during H-M loading.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consist essentially of" the recited component(s).

When ranges are used herein, such as for dose ranges, combinations and subcombinations of ranges (e.g., subranges within the disclosed range), specific embodiments therein are intended to be explicitly included. When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to embodiments of the invention.

Example Test Procedure

Figure 11:
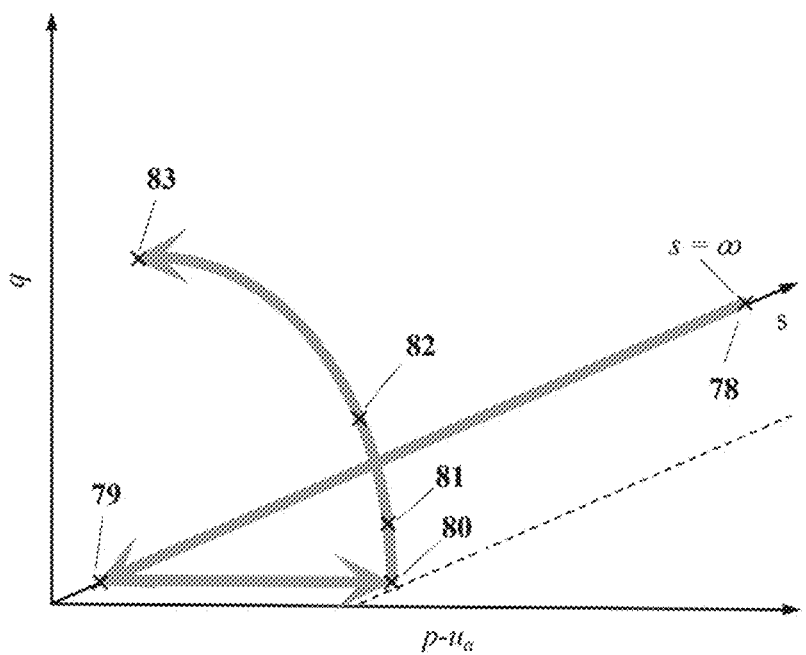
FIG. 11 is a diagram showing a stress path for an illustrative triaxial test according to an embodiment of the subject invention.

This description illustrates an example stress path by using a suction-controllable triaxial system and apparatus according to an embodiment of the subject invention. The example test procedures can include the following steps:

(1) Prepare and install a soil sample using the tailor-designed unit (e.g., as shown in FIG. 7) and then assemble the axial loading component 57, the chamber unit 12 (e.g., as shown in FIG. 3), and sample stage structure 14 (e.g., as shown in FIG. 4), of the triaxial loading unit and place the assembly on the rolling stage of an X-ray CT scanner;

(2) Connect the triaxial loading unit (e.g., as shown in FIG. 1) to the integrated cell pressure and suction-control unit (e.g., as shown in FIG. 6);

(3) Spin the triaxial loading unit on top of the rolling stage for 360 degrees to ensure that it will not collide with any parts of the X-ray CT scanner, followed by checking all electrical connections and software connection;

(4) Conduct hydro-mechanical loading to the sample and conduct X-ray scanning and imaging at certain specified, predetermined, or in-process determined points in the $(p-u_a)$-q-s space (e.g., as shown in FIG. 11);

(5) Reconstruct X-ray CT images (e.g., by reconstruction methods known in the art of computed tomography (CT) imaging) of the tested sample obtained during X-ray scanning and imaging, and arrange, review, or analyze the reconstructed images with respect to the hydro-mechanical loading to determine the micro-structure evolution of the sample during loading.

EXAMPLE

To demonstrate the capabilities and performance of the disclosed suction-controllable triaxial test system with in-situ X-ray CT scanning, a H-M loading test of unsaturated soils with in-situ X-ray micro CT scanning was carried out. FIG. 6 depicts the controlled H-M loading path used in the test.

Figure 12:
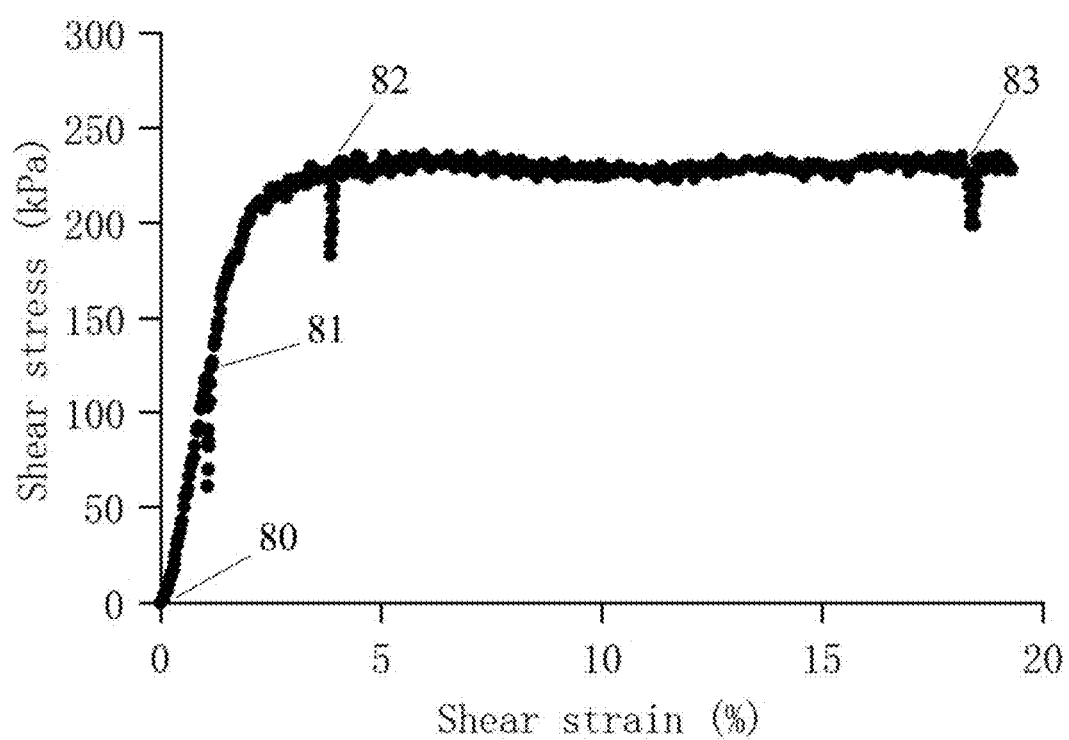
FIG. 12 is a diagram that shows a measured shear stress-shear strain curve during an actual triaxial compression test according to an embodiment of the subject invention.
Figure 13A:
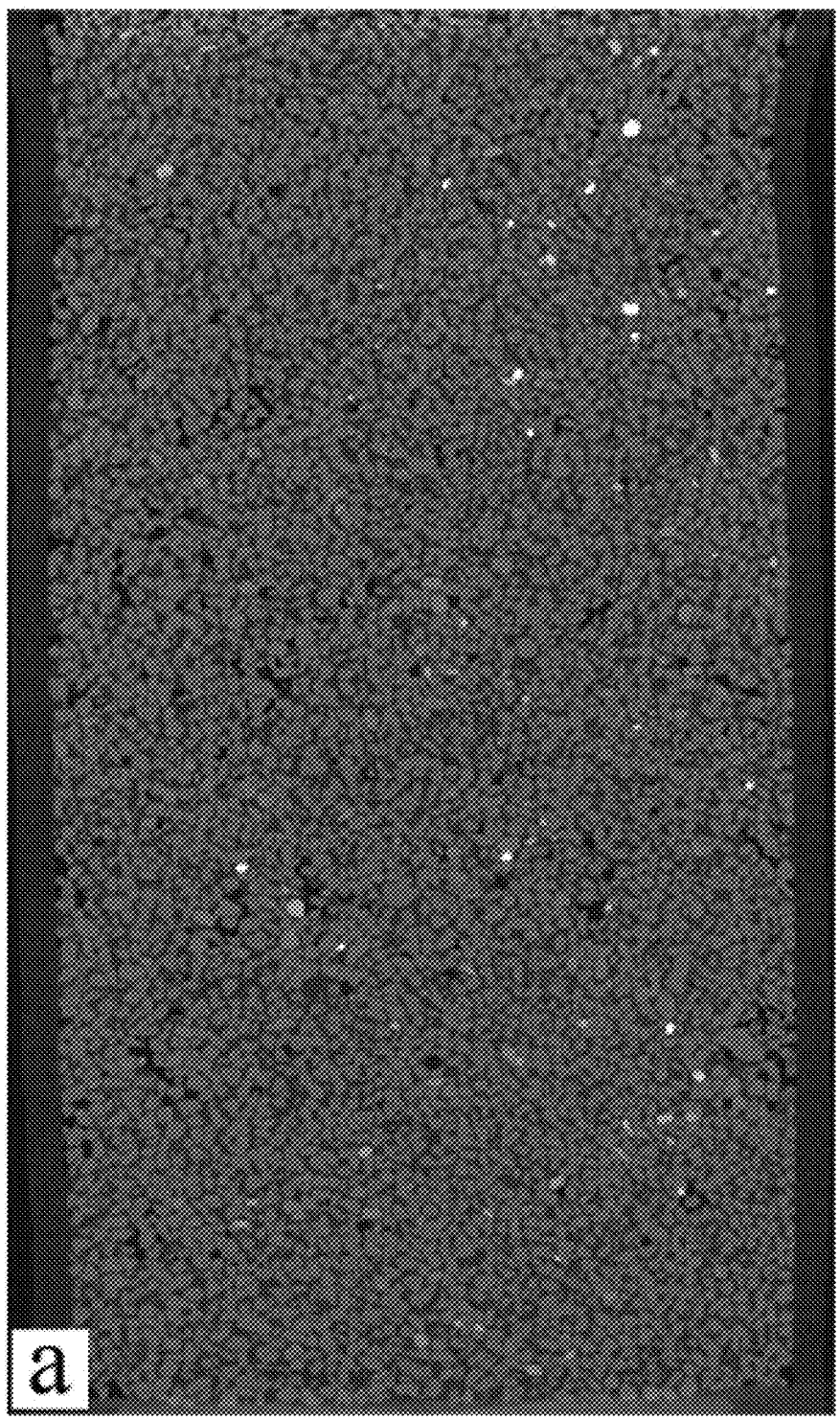
FIG. 13A-13E are captured pictures showing the microstructure of the same X-Z slice from the constructed 3D X-ray CT images of a sample at different loading stages during an actual triaxial compression test according to an embodiment of the subject invention.
Figure 13B:
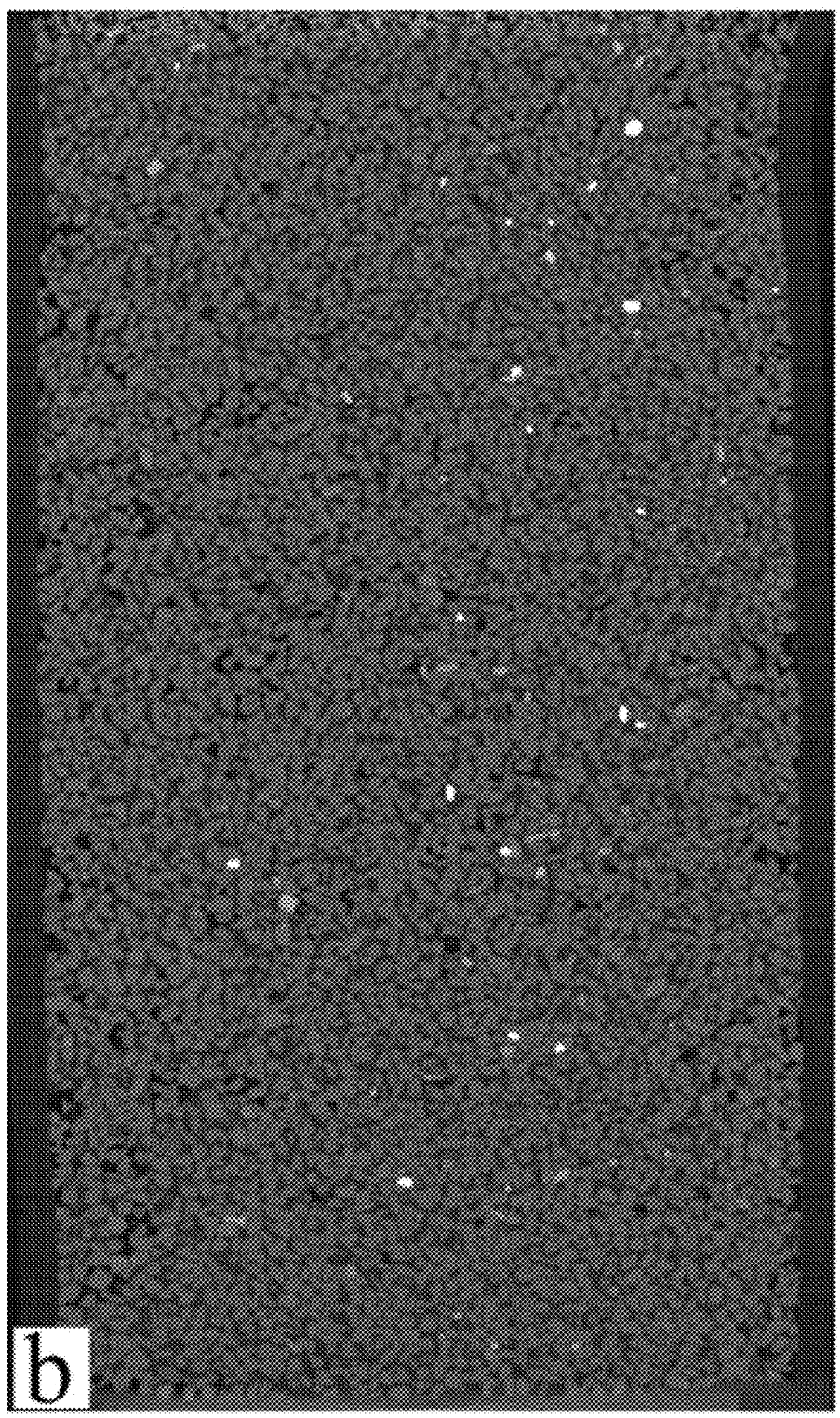
Figure 13C:
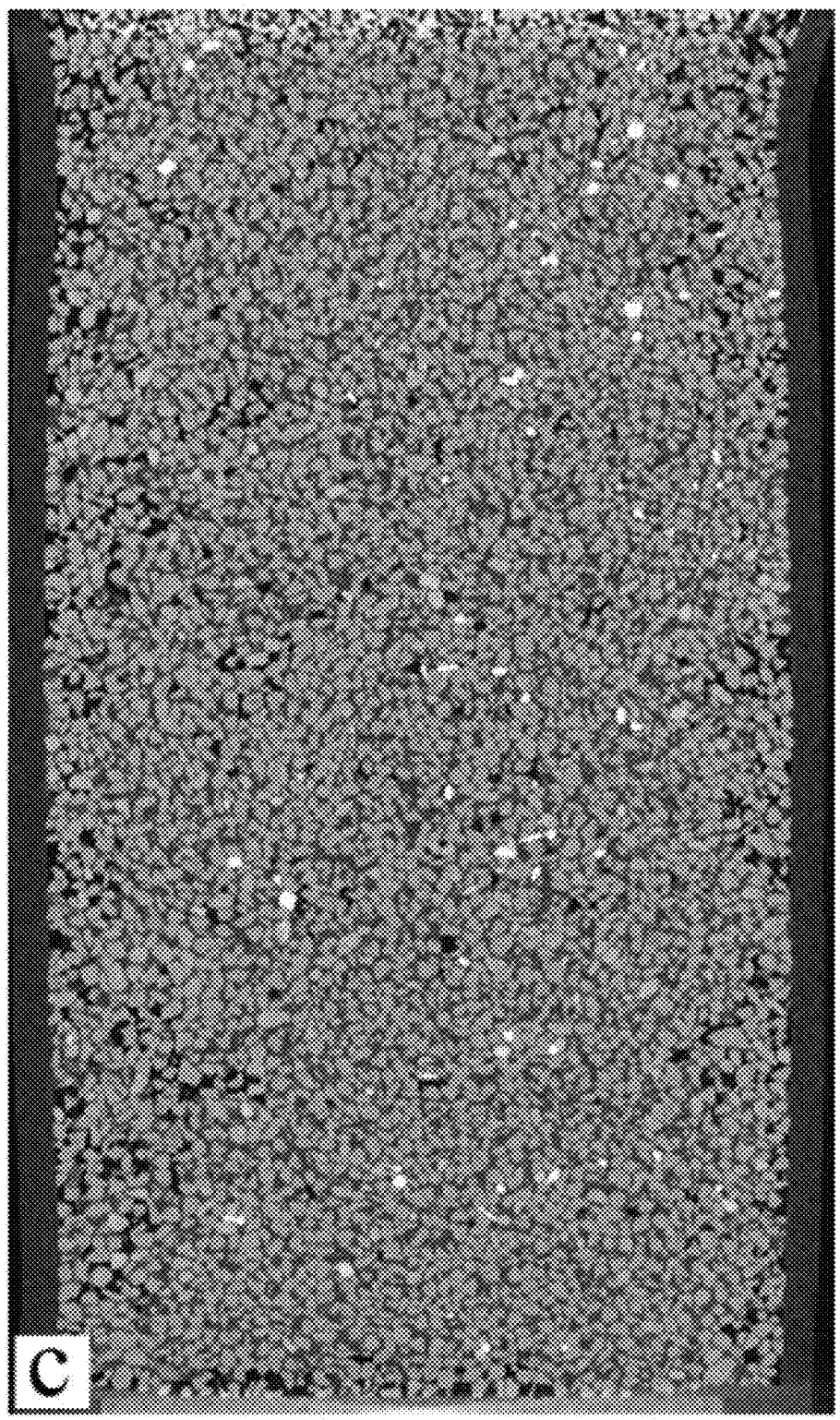
Figure 13D:
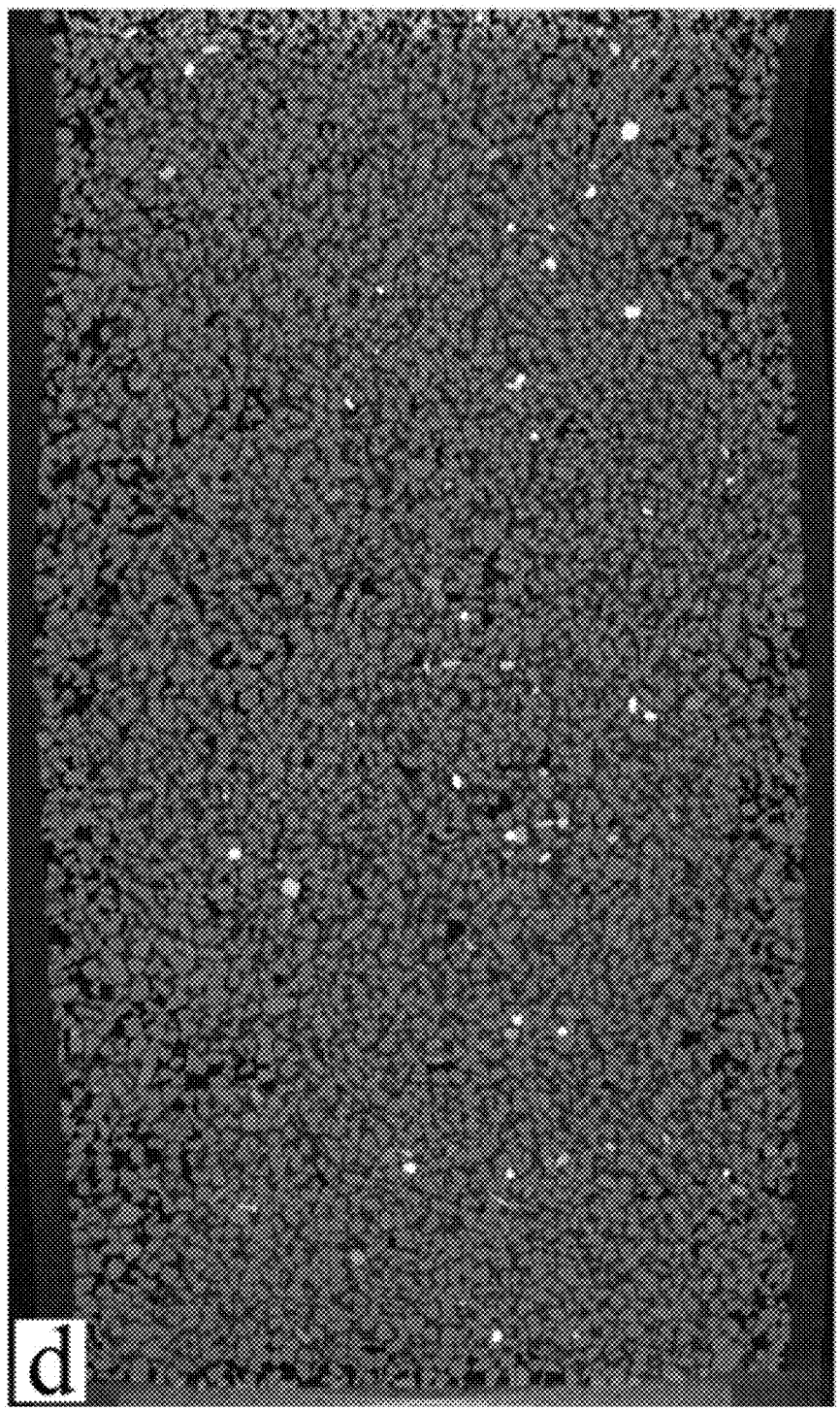
Figure 13E:
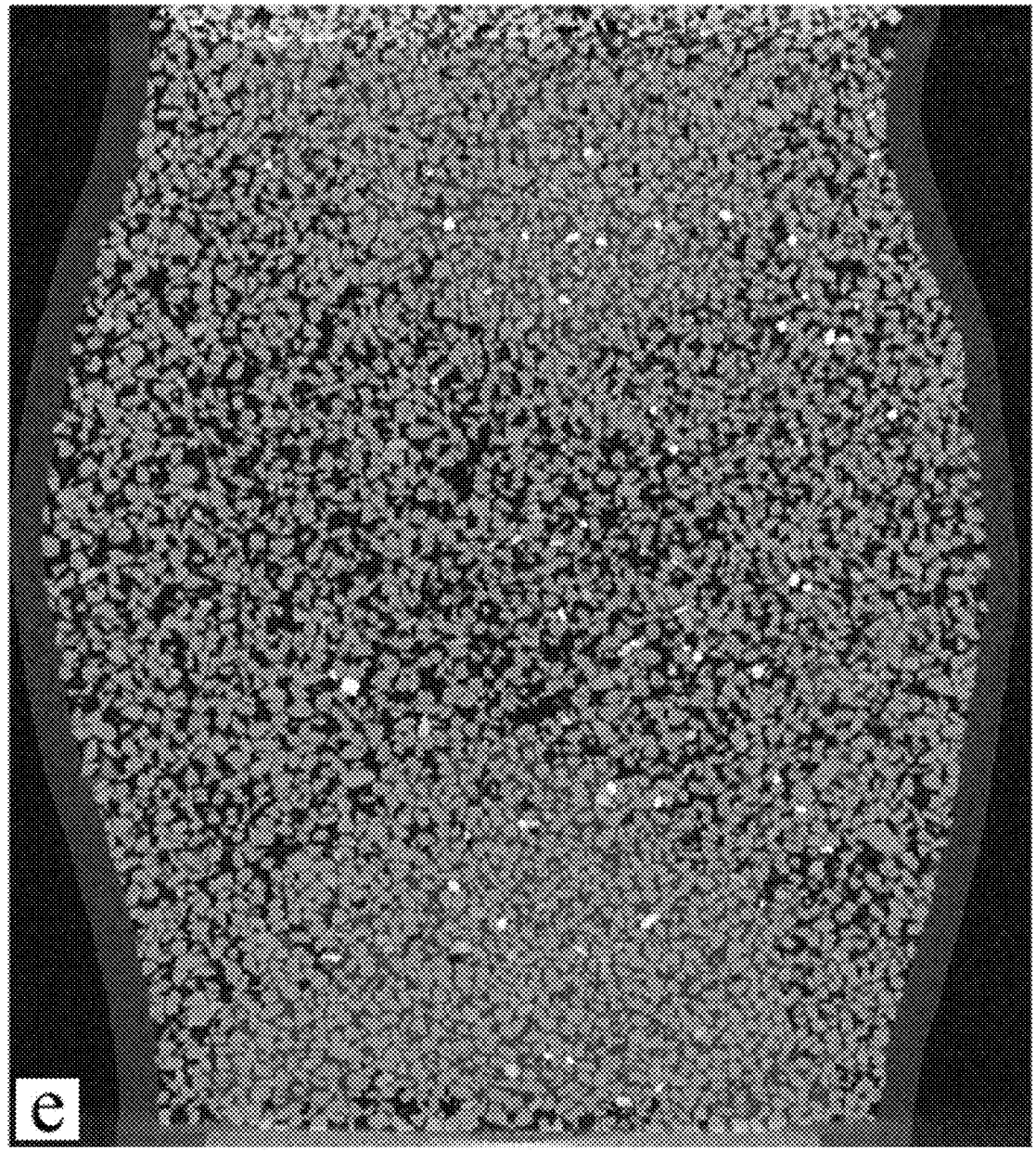
Figure 14A:
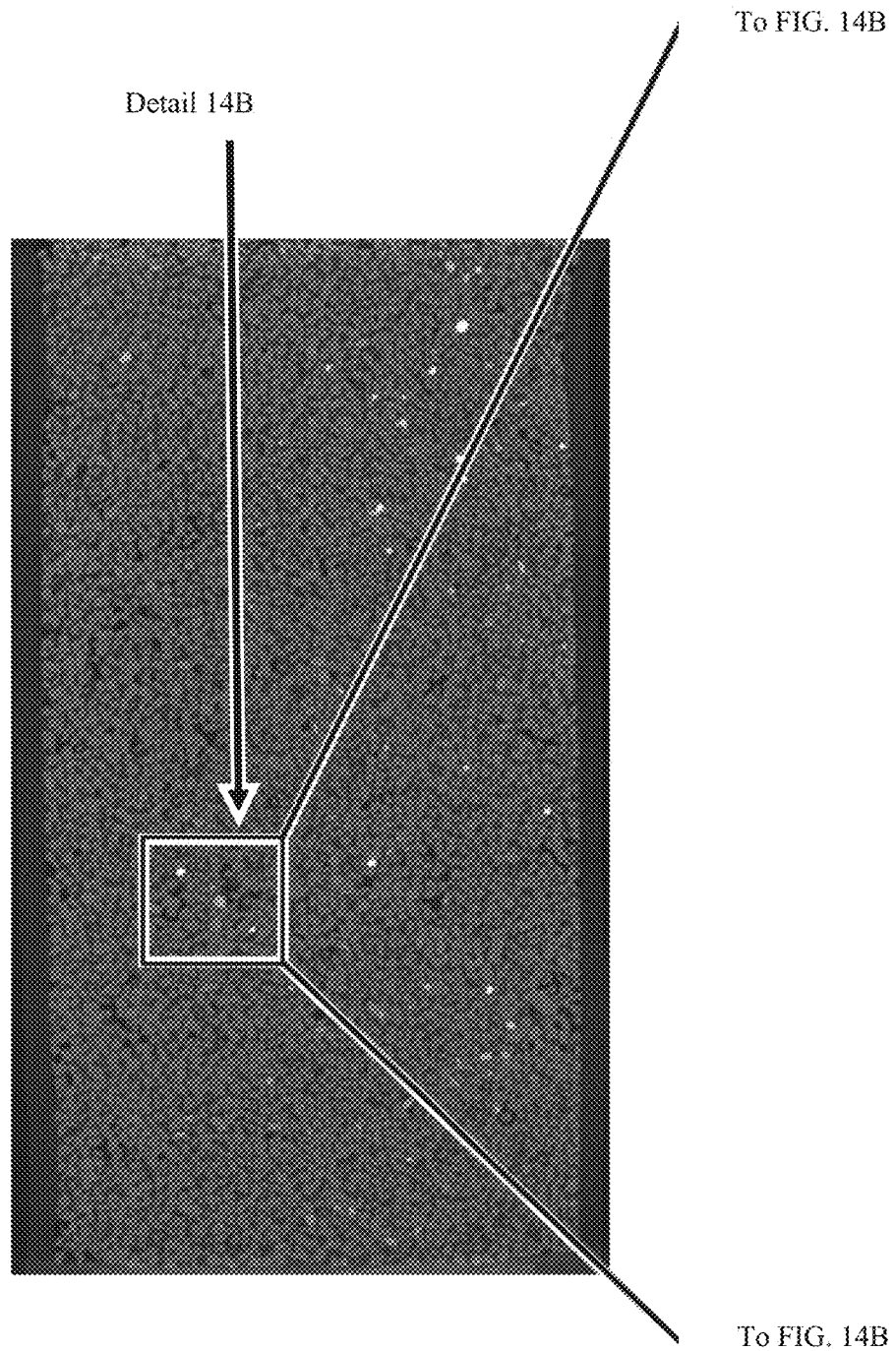
FIG. 14A is a captured x-ray CT image that shows the solid particles, pore water, and pore air of a sample during an actual triaxial compression test according to an embodiment of the subject invention. Also indicated is the location for Detail 14B within the larger image.
Figure 14B:
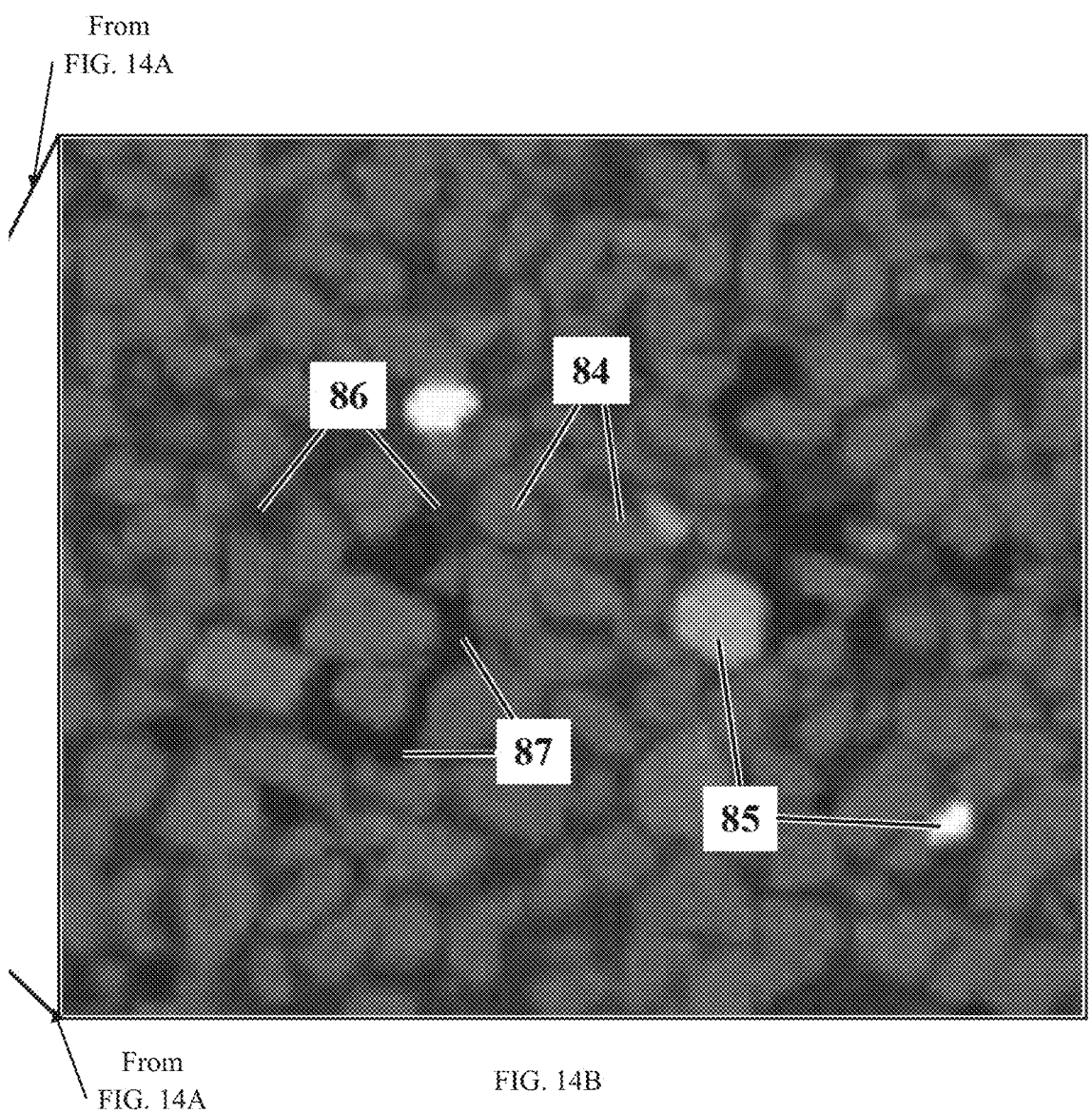
FIG. 14B is a closeup view of a captured X-ray CT image that shows the solid particles, pore water, and pore air of Detail 14B from a sample during an actual triaxial compression test according to an embodiment of the subject invention.

A Toyoura sand sample was prepared by dry deposition method using the tailor-designed mold 65 and installation components shown in FIGS. 7-9. The sample was cylindrical and had a diameter of 10 mm and a height of 20 mm. The void ratio (e) and relative density (Dr) were 0.722 and 0.633, respectively. The prepared dry sample was assumed to have an effective matric suction value of positive infinity (i.e. assumed to begin at point 78 far out along the positive s axis in FIG. 11; at this point, the sample is dry, meaning the negative pore water pressure $u_w$ is infinitesimally small while the air pressure is at atmospheric pressure, resulting $u_a$-$u_w$ becomes very large and either computationally or practically equivalent to positive infinity). After completion of sample installation, the triaxial loading unit was moved into an X-ray CT scanner for applying H-M loading and in-situ imaging simultaneously. During the H-M loading process, the sample firstly followed the matric suction reduction line to achieve saturation until the matric suction reached 0.1 kPa. The scan 79 was then conducted at this stage. After scan 79, a mechanical loading was applied: (1) the soil sample was consolidated at a confining pressure of 50 kPa and then the scan 80 was conducted after the completion of consolidation; (2) the sample was then sheared at a axial loading rate of 0.01 mm/s until reaching 18% of axial strain, during which three scans were conducted at pre-peak condition 81, peak condition 82, and critical state condition 83. A total of five scans (i.e., at points 79, 80, 81, 82, and 83 in FIG. 11) was conducted during the loading process. The stress-strain curve (FIG. 12) was obtained and images (FIG. 13) that reflected the micro-structural evolution were reconstructed. The micro-structures shown in FIGS. 13a, 13b, 13c, 13d, and 13e each, respectively, correspond to the condition at points 79, 80, 81, 82, and 83 in FIG. 11 and FIG. 12, respectively. In FIG. 13, the soil particles, pore water and pore air were clearly shown in the obtained images. The internal microstructural evolution (e.g., porosity changes, pore water and pore air distribution, particle movements, and shear band evolution) during loading were thus obtained, as shown in FIG. 13. The images in FIG. 13 are the X-Z slices at the same location of one sample during different loading stages. The brightest areas (which denotes metal solid particles) can be used as reference points. FIG. 14 is the zoomed-in area of FIG. 13a, in which the solid grains including metal grains 85 (i.e. the brightest white areas) and silica grains 84 (i.e., moderately bright silver areas), pore water 86 (i.e., gray areas), and pore air 87 (i.e., black areas) are shown clearly.

Although embodiments of this disclosed invention have been described in detail, it is understood that these embodiments are shown by way of illustration and not as limitations of the invention. Equivalents to the specific procedures and embodiments described herein will be identified and determined through routine experimentation and experimental calibration by those skilled in the art. Variations and modifications to produce such equivalents may be employed within the scope of the disclosed invention as described in the claims.

Methods described herein are in terms of the current embodiments, those skilled in the art will be able to ascertain that variation to the methods and steps or in the sequence of steps may be applied. Such variations apparent to those skilled in the art should not deviate from spirit and scope of the disclosed invention as described in the claims.

Embodiments of the subject invention include, but are not limited to, the following exemplified embodiments.

Embodiment 1. A suction-controllable triaxial test system comprising:
 a triaxial loading unit, an integrated cell pressure and suction-control unit, a strain-controlled axial loading unit, and a sample preparation and installation unit, together with associated data acquisition modules and software.

Embodiment 2. The suction-controllable triaxial test system of Embodiment 1, wherein the triaxial loading unit further comprises:
 a high resolution servo-controlled stepping motor that embeds a gear to convert rotation to linear motion;
 a high accuracy miniature load cell to monitor sample stress;
 a high accuracy LVDT to monitor sample strain;
 a loading rod and an X-ray transparent chamber;
 an air tight chamber cap that only allows vertical movements of the loading rod, and a sample stage.

Embodiment 3. The triaxial loading unit of Embodiment 2, wherein the unit is miniature in size (normally less than 400 mm in height and not larger than 120 mm in diameter) and configured and adapted to avoid any collision between the assembly and any part of an X-ray CT scanner during the spinning of a soil sample in a scanning process.

Embodiment 4. The triaxial loading unit of Embodiment 2, wherein the sample stage further comprises an embedded high AEV ceramic, a water reservoir, and a high accuracy water pressure transducer that allows negative and positive water pressure monitoring.

Embodiment 5. The triaxial loading unit of Embodiment 2, wherein the chamber and the loading rod are each, respectively, connected to a set of air pressure controlling components for independent regulation of the magnitude of confining pressure and pore-air pressure applied to a soil sample in the sample stage.

Embodiment 6. The triaxial loading unit of Embodiment 2, wherein the loading rod unit further comprises a cap connected to an external air pressure source, a hollow loading rod with a smooth exterior surface, and a connector embedded with an upward and a downward radial seal.

Embodiment 7. The triaxial loading unit of Embodiment 2, wherein the connector is connected to the soil sample during a test by a sample membrane;

Embodiment 8. The triaxial loading unit of Embodiment 6, wherein the connector is configured and adapted to move freely in a vertical direction and separate the cell pressure in the chamber from pore air pressure in the sample.

Embodiment 9. The triaxial loading unit of Embodiment 6, wherein the upward and the downward radial seals of the connector are each, respectively, 1.8 mm in diameter and are each configured and adapted to retain air in the sample and air pressure in the X-ray transparent chamber, respectively;

when the air pressure in the sample and the air pressure in the X-ray transparent chamber are of different values.

Embodiment 10. The triaxial loading unit of Embodiment 1, wherein the integrated cell pressure and suction-control unit further comprises an air pressure controlling and monitoring unit and a water pressure controlling and monitoring unit.

Embodiment 11. The triaxial loading unit of Embodiment 10, wherein the air pressure controlling and monitoring unit further comprises: three valves, a higher accuracy air pressure controller for manual or automatic control of pore air pressure, a high accuracy air pressure sensor configured and adapted to measure pore air pressure, a high range air pressure controller for manual or automatic control of confining pressure, and a high range air pressure sensor configured and adapted to measure confining pressure.

Embodiment 12. The triaxial loading unit of Embodiment 10, wherein the water pressure controlling and monitoring unit further comprises: four valves, a water pressure sensor for measuring both negative and positive pressure, an air trap with a level mark, a burette, a long flexible tube, a horizontal quartz tube with a short scale and a vertically placed long scale.

Embodiment 13. The triaxial loading unit of Embodiment 1, wherein the integrated cell pressure and suction-control unit is able to apply a wider range of matric suction comprising hydraulic loading between 0 to 500 kPa precisely through two independent modules, namely a hanging column module and an axis-translation module.

Embodiment 14. The triaxial loading unit of Embodiment 13, wherein for controlling low matric suctions between 0-10 kPa, the hanging column module is connected.

Embodiment 15. The triaxial loading unit of Embodiment 13, wherein for controlling high matric suctions between 10-500 kPa, the axis-translation module is connected.

Embodiment 16. The triaxial loading unit of Embodiment 1, wherein the homogeneous soil samples preparation and installation unit is used to connect the three components of the triaxial loading unit, namely the sample stage component, chamber component, and axial loading component.

Embodiment 17. The triaxial loading unit of Embodiment 1, wherein the soil samples are prepared directly on top of the sample stage with a mold, which includes a hole that connects to a vacuum pump to remove the air in between the membrane and the internal surface of the mold.

Embodiment 18. The triaxial loading unit of Embodiment 16, wherein the device for sample preparation and installation unit further comprises a 300 mm by 300 mm base plate, a horizontal movement controllable sliding table with a track, a wheel to control horizontal movement, and a vertical movement controllable sliding table with a track and two wheels to control vertical movement.

Embodiment 19. The triaxial loading unit of Embodiment 18, wherein the two cantilever-shaped adjustable connectors are connected to the vertical sliding table and two clamps, wherein each one of the two clamps is used to grasp the loading rod and the X-ray transparent chamber, respectively.

Embodiment 20. The triaxial loading unit of Embodiment 18, wherein the device for sample preparation and installation is constrained to provide independent concentric travel of the loading rod and the chamber, while the sample stage unit can be moved freely in any horizontal direction.

Embodiment 21. A suction-controllable triaxial test system comprising:
a triaxial loading unit comprising a strain-controlled axial loading unit;
an integrated cell pressure and suction-control unit;
a sample preparation and installation unit;
one or more data acquisition modules; and
associated software configured and adapted to operate at least the data acquisition modules.

Embodiment 22. The suction-controllable triaxial test system of Embodiment 21, wherein the triaxial loading unit further comprises:
an axial loading component comprising a high resolution servo-controlled stepping motor operably connected to a mechanism configured and adapted to convert rotation of the stepping motor to linear motion, wherein the motor and the mechanism are configured and adapted to produce a resolution better than 1 micron per step of the stepping motor;
a high accuracy miniature load cell configured and adapted to monitor sample stress at a resolution better than 0.25 N;
a high accuracy LVDT to monitor sample strain at a resolution better than 5 microns;
a loading rod assembly configured and adapted to transfer a load from the axial loading component to a soil sample;
an X-ray transparent chamber;
an air tight chamber cap that allows vertical movements while inhibiting horizontal movements of the loading rod assembly; and
a sample stage.

Embodiment 23. The suction-controllable triaxial test system of Embodiment 22, wherein the triaxial loading unit is miniature in size, less than 400 mm in height, not larger than 120 mm in diameter, and configured and adapted to avoid collision between the assembly and an X-ray CT scanner during a scanning process.

Embodiment 24. The suction-controllable triaxial test system of Embodiment 22, wherein the sample stage comprises an embedded high Air-Entry-Value (AEV) ceramic and a water reservoir; and the system further comprises a high accuracy water pressure transducer configured and adapted to provide negative and positive water pressure monitoring at a resolution better than 0.5 Pa.

Embodiment 25. The suction-controllable triaxial test system of Embodiment 22, wherein the loading rod assembly is connected to a first set of air pressure controlling components and the X-ray transparent chamber is connected to a second set of air pressure controlling components, and wherein the first set of air pressure controlling components and second set of air pressure controlling components are configured and adapted for independent regulation and control of the magnitude of a confining pressure applied to a soil sample and a pore air pressure applied to a soil sample.

Embodiment 26. The suction-controllable triaxial test system of Embodiment 22, wherein the loading rod assembly comprises a cap connected to an external air pressure source, a hollow loading rod with a smooth exterior surface, and a connector embedded with an upward radial seal and a downward radial seal.

Embodiment 27. The suction-controllable triaxial test system of claim Embodiment 26, wherein the connector is connected to the soil sample during testing by a sample membrane.

Embodiment 28. The suction-controllable triaxial test system of claim Embodiment 26, wherein the connector is configured and adapted to move freely in a vertical direction to separate the cell pressure in the chamber from the cell pore air pressure in the sample.

Embodiment 29. The suction-controllable triaxial test system of Embodiment 26, wherein the upward radial seal and the downward radial seal each are configured and adapted to seal to the smooth exterior surface of the hollow rod and maintain a first air pressure in the sample, the first air pressure different from a second air pressure in the X-ray transparent chamber.

Embodiment 30. The suction-controllable triaxial test system of Embodiment 21, further comprising an air pressure controlling and monitoring unit and a water pressure controlling and monitoring unit.

Embodiment 31. The suction-controllable triaxial test system of Embodiment 30, further comprising three air valves configured and adapted for independent control and operation, a higher accuracy air pressure controller for manual or automatic control of pore air pressure, a high accuracy air pressure sensor, a high range air pressure controller for manual or automatic control of confining pressure, and a high range air pressure sensor.

Embodiment 32. The suction-controllable triaxial test system of Embodiment 30, further comprising four water valves configured and adapted for independent control and operation, a water pressure sensor configured and adapted to measure both negative and positive pressure, an air trap with a level mark, a burette, a long flexible tube having a length between 120 cm and 150 cm, a horizontal quartz tube with a short scale at least 30 mm long with a 0.5 mm or better resolution, and a vertically placed long scale not less than 100 mm long with a 0.5 mm or better resolution.

Embodiment 33. The suction-controllable triaxial test system of Embodiment 21, comprising two or more independent modules, wherein each module, respectively, has a different technique than the other module, and wherein the each module is configured and adapted to more precisely apply a range of matric suction or hydraulic loading either above or below a specified threshold pressure.

Embodiment 34. The suction-controllable triaxial test system of claim Embodiment 33, wherein the specified threshold pressure is 10 kPa, a hanging column module is configured and adapted for controlling low matric suctions from 0-10 kPa, and an axis-translation module is configured and adapted for controlling high matric suctions from 10-500 kPa.

Embodiment 35. The suction-controllable triaxial test system of Embodiment 21, the triaxial loading unit comprising a sample stage, an X-ray transparent chamber, and a mold directly on top of the sample stage comprising a hole connected to a vacuum pump configured and adapted to remove air from between a membrane and an internal surface of the mold.

Embodiment 36. The suction-controllable triaxial test system of claim Embodiment 35, comprising:
  a base plate measuring at least about 300 mm by 300 mm in two orthogonal directions;
  a horizontal movement controllable sliding table with a track and a driver configured and adapted to control horizontal movement;
  a vertical movement controllable sliding table with a track and one or more drivers configured and adapted to control vertical movement;
  two cantilever-shaped adjustable connectors connected to the vertical sliding table; and
  two clamps configured and adapted to grasp the loading rod and the X-ray transparent chamber, respectively;
  wherein the homogeneous soil samples preparation and installation unit is configured and adapted for (1) independent concentric travel of the loading rod with respect to the chamber, and (2) independent horizontal movement of the sample stage.

Embodiment 37. A suction-controllable triaxial test system comprising:
  a triaxial loading unit that is miniature in size, less than 400 mm in height, not larger than 120 mm in diameter, and configured and adapted to avoid collision between the assembly and an X-ray CT scanner during a scanning process, the triaxial loading unit comprising a strain-controlled axial loading unit;
  an integrated cell pressure and suction-control unit;
  a sample preparation and installation unit;
  one or more data acquisition modules;
  associated software configured and adapted to operate at least the data acquisition modules;
  an axial loading component comprising a high resolution servo-controlled stepping motor operably connected to a mechanism configured and adapted to convert rotation of the stepping motor to linear motion, wherein the motor and the mechanism are configured and adapted to produce a resolution better than 1 micron per step of the stepping motor;
  a high accuracy miniature load cell configured and adapted to monitor sample stress at a resolution better than 0.25 N;
  a high accuracy LVDT to monitor sample strain at a resolution better than 5 microns;
  a loading rod assembly configured and adapted to transfer a load from the axial loading component to a soil sample;
  an X-ray transparent chamber;
  an air tight chamber cap that allows vertical movements while inhibiting horizontal movements of the loading rod assembly; and
  a sample stage comprising an embedded high Air-Entry-Value (AEV) ceramic and a water reservoir; and
  a high accuracy water pressure transducer configured and adapted to provide negative and positive water pressure monitoring at a resolution better than 0.5 Pa;
  wherein the loading rod assembly is connected to a first set of air pressure controlling components and the X-ray transparent chamber is connected to a second set of air pressure controlling components, and wherein the first set of air pressure controlling components and second set of air pressure controlling components are configured and adapted for independent regulation and control of the magnitude of a confining pressure applied to a soil sample and a pore air pressure applied to a soil sample;
  wherein the loading rod assembly comprises a cap connected to an external air pressure source, a hollow loading rod with a smooth exterior surface, and a connector embedded with an upward radial seal and a downward radial seal;
  wherein the connector is connected to the soil sample during testing by a sample membrane;
  wherein the connector is configured and adapted to move freely in a vertical direction to separate the cell pressure in the chamber from the cell pore air pressure in the sample; and
  wherein the upward radial seal and the downward radial seal each are configured and adapted to seal to the smooth exterior surface of the hollow rod and maintain a first air pressure in the sample, the first air pressure different from a second air pressure in the X-ray transparent chamber.

Embodiment 38. The suction-controllable triaxial test system of Embodiment 37, further comprising:

an air pressure controlling and monitoring unit;
a water pressure controlling and monitoring unit;
three air valves configured and adapted for independent control and operation;
a higher accuracy air pressure controller for manual or automatic control of pore air pressure;
a high accuracy air pressure sensor;
a high range air pressure controller for manual or automatic control of confining pressure;
a high range air pressure sensor;
four water valves configured and adapted for independent control and operation;
a water pressure sensor configured and adapted to measure both negative and positive pressure;
an air trap with a level mark;
a burette;
a long flexible tube having a length between 120 cm and 150 cm;
a horizontal quartz tube with a short scale at least 30 mm long with a 0.5 mm or better resolution;
a vertically placed long scale not less than 100 mm long with a 0.5 mm or better resolution;
a hanging column module configured and adapted for controlling low matric suctions from 0-10 kPa;
an axis-translation module is configured and adapted for controlling high matric suctions from 10-500 kPa.

Embodiment 39. The suction-controllable triaxial test system of Embodiment 38,
the triaxial loading unit comprising a sample stage, an X-ray transparent chamber, and a mold directly on top of the sample stage comprising a hole connected to a vacuum pump configured and adapted to remove air from between a membrane and an internal surface of the mold;
the system comprising:
a base plate measuring at least about 300 mm by 300 mm in two orthogonal directions;
a horizontal movement controllable sliding table with a track and a driver configured and adapted to control horizontal movement;
a vertical movement controllable sliding table with a track and one or more drivers configured and adapted to control vertical movement;
two cantilever-shaped adjustable connectors connected to the vertical sliding table; and
two clamps configured and adapted to grasp the loading rod and the X-ray transparent chamber, respectively;
wherein the homogeneous soil samples preparation and installation unit is configured and adapted for (1) independent concentric travel of the loading rod with respect to the chamber, and (2) independent horizontal movement of the sample stage.

Embodiment 40. A method for capturing in-situ microstructure evolution of a soil sample during triaxial load testing, the method comprising:
preparing and installing a soil sample into a triaxial loading unit using the suction-controllable triaxial test system of claim 2;
conducting X-ray scanning and imaging simultaneously with conducting triaxial hydro-mechanical loading of the sample; and
reconstructing one or more images of the tested sample obtained at two or more specified points in a $((p-u_a), q, s)$ space during the X-ray scanning and imaging, to capture the in-situ micro-structure evolution of the soil sample during triaxial load testing.

Embodiment 41. A method for capturing in-situ microstructure evolution of a soil sample during triaxial load testing, the method comprising:
preparing and installing a soil sample into a triaxial loading unit using a mold mounted directly on top of a sample stage;
assembling the soil sample into the sample stage component;
assembling the sample stage component containing the soil sample with a chamber component and an axial loading component to form a;
mounting the triaxial loading unit onto a rolling stage of an X-ray CT scanner;
connecting the triaxial loading unit to an integrated cell pressure and suction-control unit;
rotating the rolling stage and the triaxial loading unit to conduct X-ray scanning and imaging while conducting triaxial hydro-mechanical loading of the sample; and
reconstructing one or more images of the tested sample obtained at one or more specified points in a $((p-u_a), q, s)$ space during the X-ray scanning and imaging, to capture the in-situ micro-structure evolution of the soil sample during triaxial load testing.

REFERENCES

1. Ando, Edward. 2015. "Experimental Investigation of Microstructural Changes in Deforming Granular Media Using X-Ray Tomography." Mechanics.
2. Cheng, Zhuang, and Jianfeng Wang. 2018. "A Particle-Tracking Method for Experimental Investigation of Kinematics of Sand Particles under Triaxial Compression." Powder Technology 328: 436-51. https://doi.org/10.1016/j.powtec.2017.12.071.
3. Higo, Yosuke, Fusao Oka, Tomohiro Sato, Yoshiki Matsushima, and Sayuri Kimoto. 2013. "Investigation of Localized Deformation in Partially Saturated Sand under Triaxial Compression Using Microfocus X-Ray CT with Digital Image Correlation." Soils and Foundations 53 (2): 181-98. https://doi.org/10.1016/j.sandf.2013.02.001.
4. Khaddour, Ghonwa, Ismael Riedel, Edward Ando, Pascal Charrier, Pierre Bésuelle, Jacques Desrues, Gioacchino Viggiani, and Simon Salager. 2018. "Grain-Scale Characterization of Water Retention Behaviour of Sand Using X-Ray CT." Acta Geotechnica 13 (3): 497-512. https://doi.org/10.1007/s11440-018-0628-7.
5. Manahiloh, Kalehiwot Nega, and Christopher L. Meehan. 2017. "Determining the Soil Water Characteristic Curve and Interfacial Contact Angle from Microstructural Analysis of X-Ray CT Images." Journal of Geotechnical and Geoenvironmental Engineering 143 (8): 1-11. https://doi.org/10.1061/(ASCE)GT.1943-5606.0001677.
6. Mohsin Thakur, Mohmad, Dayakar Penumadu, and Constantin Bauer. 2020. "Capillary Suction Measurements in Granular Materials and Direct Numerical Simulations Using X-Ray Computed Tomography Microstructure." Journal of Geotechnical and Geoenvironmental Engineering 146 (1): 1-13. https://doi.org/10.1061/(ASCE)GT.1943-5606.0002194.
7. Wang, J.-P., E. Andó, P. Charrier, S. Salager, P. Lambert, and B. François. 2019. "Micro-Scale Investigation of Unsaturated Sand in Mini-Triaxial Shearing Using X-Ray CT." Géotechnique Letters 9 (4): 269-77. https://doi.org/10.1680/jgele.18.00214.
8. Wang, Ji Peng, Pierre Lambert, Tim De Kock, Veerle Cnudde, and Bertrand Francois. 2019. "Investigation of the Effect of Specific Interfacial Area on Strength of Unsaturated Granular Materials by X-Ray Tomography." Acta Geotechnica 14 (5): 1545-59. https://doi.org/10.1007/s11440-019-00765-2.

We claim:

1. A suction-controllable triaxial test system comprising:
a triaxial loading unit comprising a strain-controlled axial loading unit;
an integrated cell pressure and suction-control unit;
a sample preparation and installation unit;
one or more data acquisition modules;
associated software configured and adapted to operate at least the data acquisition modules; and
two or more independent modules,
wherein each independent module, respectively, has a technique different from the other independent module, and wherein each independent module is configured and adapted to apply a range of matric suction or hydraulic loading either above or below a specified threshold pressure.

2. The suction-controllable triaxial test system of claim 1, wherein the triaxial loading unit further comprises:
an axial loading component comprising a high resolution servo-controlled stepping motor operably connected to a mechanism configured and adapted to convert rotation of the stepping motor to linear motion, wherein the motor and the mechanism are configured and adapted to produce a resolution better than 1 micron per step of the stepping motor;
a high accuracy miniature load cell configured and adapted to monitor sample stress at a resolution better than 0.25 N;
a high accuracy LVDT to monitor sample strain at a resolution better than 5 microns;
a loading rod assembly configured and adapted to transfer a load from the axial loading component to a soil sample;
an X-ray transparent chamber;
an air tight chamber cap that allows vertical movements while inhibiting horizontal movements of the loading rod assembly; and
a sample stage.

3. The suction-controllable triaxial test system of claim 2, wherein the triaxial loading unit is miniature in size, less than 400 mm in height, not larger than 120 mm in diameter, and configured and adapted to inhibit collision between the assembly and an X-ray CT scanner during a scanning process.

4. The suction-controllable triaxial test system of claim 2, wherein the sample stage comprises an embedded high Air-Entry-Value (AEV) ceramic and a water reservoir; and the system further comprises a high accuracy water pressure transducer configured and adapted to provide negative and positive water pressure monitoring at a resolution better than 0.5 Pa.

5. The suction-controllable triaxial test system of claim 2, wherein the loading rod assembly is connected to a first set of air pressure controlling components and the X-ray transparent chamber is connected to a second set of air pressure controlling components, and wherein the first set of air pressure controlling components and second set of air pressure controlling components are configured and adapted for independent regulation and control of the magnitude of a confining pressure applied to a soil sample and a pore air pressure applied to a soil sample.

6. The suction-controllable triaxial test system of claim 2, wherein the loading rod assembly comprises a cap connected to an external air pressure source, a hollow loading rod with a smooth exterior surface, and a connector embedded with an upward radial seal and a downward radial seal.

7. The suction-controllable triaxial test system of claim 6, wherein the connector is connected to the soil sample during testing by a sample membrane.

8. The suction-controllable triaxial test system of claim 6, wherein the connector is configured and adapted to move freely in a vertical direction to separate the cell pressure in the chamber from the cell pore air pressure in the sample.

9. The suction-controllable triaxial test system of claim 6, wherein the upward radial seal and the downward radial seal each is configured and adapted to seal to the smooth exterior surface of the hollow rod and maintain a first air pressure in the sample, the first air pressure different from a second air pressure in the X-ray transparent chamber.

10. The suction-controllable triaxial test system of claim 1, further comprising an air pressure controlling and monitoring unit and a water pressure controlling and monitoring unit.

11. The suction-controllable triaxial test system of claim 10, further comprising three air valves configured and adapted for independent control and operation, a higher accuracy air pressure controller for manual or automatic control of pore air pressure, a high accuracy air pressure sensor, a high range air pressure controller for manual or automatic control of confining pressure, and a high range air pressure sensor.

12. The suction-controllable triaxial test system of claim 10, further comprising four water valves configured and adapted for independent control and operation, a water pressure sensor configured and adapted to measure both negative and positive pressure, an air trap with a level mark, a burette, a long flexible tube having a length between 120 cm and 150 cm, a horizontal quartz tube with a short scale at least 30 mm long with a 0.5 mm or better resolution, and a vertically placed long scale not less than 100 mm long with a 0.5 mm or better resolution.

13. The suction-controllable triaxial test system of claim 1, wherein the specified threshold pressure is 10 kPa, and the independent modules comprise a hanging column module that is configured and adapted for controlling low matric suctions from 0-10 kPa, and an axis-translation module that is configured and adapted for controlling high matric suctions from 10-500 kPa.

14. The suction-controllable triaxial test system of claim 1, the triaxial loading unit comprising a sample stage, an X-ray transparent chamber, and a mold directly on top of the sample stage comprising a hole connected to a vacuum pump configured and adapted to remove air from between a membrane and an internal surface of the mold.

15. The suction-controllable triaxial test system of claim 14, comprising:
a base plate measuring at least about 300 mm by 300 mm in two orthogonal directions;
a horizontal movement controllable sliding table with a track and a driver configured and adapted to control a horizontal movement;
a vertical movement controllable sliding table with a track and one or more drivers configured and adapted to control a vertical movement;
two cantilever-shaped adjustable connectors connected to the vertical sliding table; and
two clamps configured and adapted to grasp the loading rod and the X-ray transparent chamber, respectively;
wherein the homogeneous soil samples preparation and installation unit is configured and adapted for (1) independent concentric travel of the loading rod with respect to the chamber, and (2) an independent horizontal movement of the sample stage.

16. A suction-controllable triaxial test system comprising:
a triaxial loading unit that is miniature in size, less than 400 mm in height, not larger than 120 mm in diameter, and configured and adapted to inhibit collision between the assembly and an X-ray CT scanner during a scanning process, the triaxial loading unit comprising a strain-controlled axial loading unit;
an integrated cell pressure and suction-control unit;
a sample preparation and installation unit;
one or more data acquisition modules;
associated software configured and adapted to operate at least the data acquisition modules;
an axial loading component comprising a high resolution servo-controlled stepping motor operably connected to a mechanism configured and adapted to convert rotation of the stepping motor to linear motion, wherein the motor and the mechanism are configured and adapted to produce a resolution better than 1 micron per step of the stepping motor;
a high accuracy miniature load cell configured and adapted to monitor sample stress at a resolution better than 0.25 N;
a high accuracy LVDT to monitor sample strain at a resolution better than 5 microns;
a loading rod assembly configured and adapted to transfer a load from the axial loading component to a soil sample;
an X-ray transparent chamber;
an air tight chamber cap that allows vertical movements while inhibiting horizontal movements of the loading rod assembly; and
a sample stage comprising an embedded high Air-Entry-Value (AEV) ceramic and a water reservoir; and
a high accuracy water pressure transducer configured and adapted to provide negative and positive water pressure monitoring at a resolution better than 0.5 Pa;
wherein the loading rod assembly is connected to a first set of air pressure controlling components and the X-ray transparent chamber is connected to a second set of air pressure controlling components, and wherein the first set of air pressure controlling components and second set of air pressure controlling components are configured and adapted for independent regulation and control of the magnitude of a confining pressure applied to a soil sample and a pore air pressure applied to a soil sample;
wherein the loading rod assembly comprises a cap connected to an external air pressure source, a hollow loading rod with a smooth exterior surface, and a connector embedded with an upward radial seal and a downward radial seal;
wherein the connector is connected to the soil sample during testing by a sample membrane;
wherein the connector is configured and adapted to move freely in a vertical direction to separate the cell pressure in the chamber from the cell pore air pressure in the sample; and
wherein the upward radial seal and the downward radial seal each are configured and adapted to seal to the smooth exterior surface of the hollow rod and maintain a first air pressure in the sample, the first air pressure different from a second air pressure in the X-ray transparent chamber.

17. The suction-controllable triaxial test system of claim 16, further comprising:
an air pressure controlling and monitoring unit;
a water pressure controlling and monitoring unit;
three air valves configured and adapted for independent control and operation;
a higher accuracy air pressure controller for manual or automatic control of pore air pressure;
a high accuracy air pressure sensor;
a high range air pressure controller for manual or automatic control of confining pressure;
a high range air pressure sensor;
four water valves configured and adapted for independent control and operation;
a water pressure sensor configured and adapted to measure both negative and positive pressure;
an air trap with a level mark;
a burette;
a long flexible tube having a length between 120 cm and 150 cm;
a horizontal quartz tube with a short scale at least 30 mm long with a 0.5 mm or better resolution;
a vertically placed long scale not less than 100 mm long with a 0.5 mm or better resolution;
a hanging column module configured and adapted for controlling low matric suctions from 0-10 kPa; and
an axis-translation module is configured and adapted for controlling high matric suctions from 10-500 kPa.

18. The suction-controllable triaxial test system of claim 17,
the triaxial loading unit comprising a sample stage, an X-ray transparent chamber, and a mold directly on top of the sample stage comprising a hole connected to a vacuum pump configured and adapted to remove air from between a membrane and an internal surface of the mold;
the system comprising:
a base plate measuring at least about 300 mm by 300 mm in two orthogonal directions;
a horizontal movement controllable sliding table with a track and a driver configured and adapted to control a horizontal movement;
a vertical movement controllable sliding table with a track and one or more drivers configured and adapted to control a vertical movement;
two cantilever-shaped adjustable connectors connected to the vertical sliding table; and
two clamps configured and adapted to grasp the loading rod and the X-ray transparent chamber, respectively;
wherein the homogeneous soil samples preparation and installation unit is configured and adapted for (1) independent concentric travel of the loading rod with respect to the chamber, and (2) an independent horizontal movement of the sample stage.

19. A method for capturing in-situ micro-structure evolution of a soil sample during triaxial load testing, the method comprising:
preparing and installing, by a suction-controllable triaxial test system, a soil sample into a triaxial loading unit of a suction-controllable triaxial test system, wherein the triaxial loading unit includes a strain-controlled axial loading unit and two or more independent modules, wherein each module, respectively, has a different technique than the other module, and wherein each independent module is configured and adapted to more precisely apply a range of matric suction or hydraulic loading either above or below a specified threshold pressure;

conducting X-ray scanning and imaging simultaneously with conducting triaxial hydro-mechanical loading of the sample; and reconstructing one or more images of the tested sample obtained at two or more specified points in a (($p-u_a$), q, s) space during the X-ray scanning and imaging, to capture the in-situ micro-structure evolution of the soil sample during triaxial load testing.

20. The method of claim 19, wherein the suction-controllable triaxial test system comprises:
a triaxial loading unit comprising a strain-controlled axial loading unit;
an integrated cell pressure and suction-control unit;
a sample preparation and installation unit;
one or more data acquisition modules; and
associated software configured and adapted to operate at least the data acquisition modules.

21. The method of claim 20, wherein the triaxial loading unit further comprises:
an axial loading component comprising a high resolution servo-controlled stepping motor operably connected to a mechanism configured and adapted to convert rotation of the stepping motor to linear motion, wherein the motor and the mechanism are configured and adapted to produce a resolution better than 1 micron per step of the stepping motor;
a high accuracy miniature load cell configured and adapted to monitor sample stress at a resolution better than 0.25 N;
a high accuracy LVDT to monitor sample strain at a resolution better than 5 microns;
a loading rod assembly configured and adapted to transfer a load from the axial loading component to a soil sample;
an X-ray transparent chamber;
an air tight chamber cap that allows vertical movements while inhibiting horizontal movements of the loading rod assembly; and
a sample stage.

* * * * *